United States Patent
Khanal et al.

(10) Patent No.: US 11,878,280 B2
(45) Date of Patent: *Jan. 23, 2024

(54) MICROCAPSULES COMPRISING NATURAL MATERIALS

(71) Applicant: TRUCAPSOL LLC, Bethlehem, PA (US)

(72) Inventors: Anil Khanal, Allentown, PA (US); Praveen Bachawala, Allentown, PA (US); Jiten Dihora, Center Valley, PA (US)

(73) Assignee: TRUCAPSOL LLC, Bethlehem, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/724,141

(22) Filed: Apr. 19, 2022

(65) Prior Publication Data

US 2023/0330615 A1 Oct. 19, 2023

(51) Int. Cl.

| | |
|---|---|
| *B01J 13/16* | (2006.01) |
| *A23L 27/00* | (2016.01) |
| *A61K 8/11* | (2006.01) |
| *A61K 8/87* | (2006.01) |
| *A61Q 5/02* | (2006.01) |
| *A61Q 5/12* | (2006.01) |
| *A61Q 13/00* | (2006.01) |
| *A61Q 15/00* | (2006.01) |
| *A61Q 19/10* | (2006.01) |
| *C08G 18/28* | (2006.01) |
| *C08G 18/58* | (2006.01) |
| *C08K 5/17* | (2006.01) |
| *C11B 9/00* | (2006.01) |
| *C11D 3/00* | (2006.01) |
| *C11D 3/50* | (2006.01) |
| *C08F 222/06* | (2006.01) |
| *C08L 1/02* | (2006.01) |

(52) U.S. Cl.
CPC ............. *B01J 13/16* (2013.01); *A23L 27/72* (2016.08); *A61K 8/11* (2013.01); *A61K 8/87* (2013.01); *A61Q 5/02* (2013.01); *A61Q 5/12* (2013.01); *A61Q 13/00* (2013.01); *A61Q 15/00* (2013.01); *A61Q 19/10* (2013.01); *C08G 18/289* (2013.01); *C08G 18/581* (2013.01); *C08K 5/17* (2013.01); *C11B 9/00* (2013.01); *C11D 3/001* (2013.01); *C11D 3/505* (2013.01); *C08F 222/06* (2013.01); *C08L 1/02* (2013.01)

(58) Field of Classification Search
CPC . B01J 13/16; A23L 27/72; A61K 8/11; A61K 8/87; A61Q 5/02; A61Q 13/00; A61Q 15/00; A61Q 19/10; C08G 18/289; C08G 18/581; C08K 5/17; C11B 9/00; C11D 3/001; C11D 3/505; C08F 222/06; C08L 1/02

See application file for complete search history.

(56) References Cited

U.S. PATENT DOCUMENTS

| | | |
|---|---|---|
| 2,573,900 A | 11/1951 | Freeman |
| 3,345,358 A | 10/1967 | Inklaar |
| 3,819,838 A | 6/1974 | Smith et al. |
| 3,870,542 A | 3/1975 | Ida et al. |
| 4,076,774 A | 2/1978 | Short |
| 4,626,471 A | 12/1986 | Chao |
| 4,818,539 A | 4/1989 | Shaw et al. |
| 5,015,527 A | 5/1991 | Chao |
| 5,126,151 A | 6/1992 | Bodor et al. |
| 5,227,446 A | 7/1993 | Denzinger et al. |
| 5,550,189 A | 8/1996 | Qin et al. |
| 5,574,179 A | 11/1996 | Wahl et al. |
| 5,601,760 A | 2/1997 | Rosenberg |
| 5,837,747 A | 11/1998 | Soon-Shiong et al. |
| 6,248,909 B1 | 6/2001 | Akimoto et al. |

(Continued)

FOREIGN PATENT DOCUMENTS

| | | |
|---|---|---|
| CA | 1049335 A | 2/1979 |
| CN | 114539887 A | 5/2022 |

(Continued)

OTHER PUBLICATIONS

Adhesives Magazine (2016). Sartomer: Acrylate Oliogmer. Available at: https://www.adhesivesmag.com/articles/94922-sartomer-acrylate-oligomer.

(Continued)

*Primary Examiner* — Doan T Phan
(74) *Attorney, Agent, or Firm* — CAESAR RIVISE, PC

(57) ABSTRACT

A method is disclosed for preparing a composition including controlled release particles includes: (a) preparing an oil phase including at least one hydrophobic active ingredient, at least one isocyanate, at least one epoxy, at least one organofunctional silane, optionally at least one pre-reacted natural material resin, and optionally a plasticizer; (b) preparing an aqueous phase comprising an emulsifier; (c) combining the oil phase and the aqueous phase to provide an aqueous suspension; (d) adding at least one amine moiety containing material to provide a barrier; (e) heating; (f) adding a natural material to provide a microcapsule having hydroxyl moieties or amine moieties on a surface thereof; (g) adding an aldehyde to react with the surface moieties; and (h) adding structuring agents to provide the controlled release particles homogeneously suspended in an aqueous dispersion. The composition is also disclosed.

23 Claims, No Drawings

(56) References Cited

U.S. PATENT DOCUMENTS

| | | | |
|---|---|---|---|
| 6,465,016 B2 | 10/2002 | Parikh et al. |
| 6,572,919 B2 | 6/2003 | Westland et al. |
| 6,596,073 B1 | 7/2003 | Nyssen et al. |
| 6,855,335 B2 | 2/2005 | Seok et al. |
| 7,431,986 B2 | 10/2008 | Van Lengerich et al. |
| 8,900,495 B2 | 12/2014 | Pacorel et al. |
| 8,993,041 B2 | 3/2015 | To et al. |
| 9,205,395 B2 | 12/2015 | Yan |
| 9,332,774 B2 | 5/2016 | Nakhasi et al. |
| 9,416,050 B2 | 8/2016 | Seidl et al. |
| 9,427,719 B2 | 8/2016 | Viaud-Massuard et al. |
| 9,714,397 B2 | 7/2017 | Feng et al. |
| 9,937,477 B2 | 4/2018 | Zhang et al. |
| 9,944,886 B2 | 4/2018 | Hitchcock et al. |
| 9,993,401 B2 | 6/2018 | Barnett et al. |
| 10,188,593 B2 | 1/2019 | Dihora et al. |
| 11,179,302 B2 | 11/2021 | Dardelle |
| 11,344,502 B1 | 5/2022 | Dihora et al. |
| 11,465,117 B2 | 10/2022 | Bachawala et al. |
| 11,484,857 B2 | 11/2022 | Bachawala et al. |
| 11,542,392 B1 | 1/2023 | Multari |
| 11,547,978 B2 | 1/2023 | Bachawala et al. |
| 11,571,674 B1 | 2/2023 | Dihora et al. |
| 2002/0169233 A1 | 11/2002 | Schwantes |
| 2004/0017017 A1 | 1/2004 | Van Lengerich et al. |
| 2004/0033264 A1 | 2/2004 | Sawhney |
| 2005/0272628 A1 | 12/2005 | Meli et al. |
| 2005/0276831 A1 | 12/2005 | Dihora et al. |
| 2007/0122455 A1 | 5/2007 | Myers et al. |
| 2008/0085297 A1 | 4/2008 | Dave et al. |
| 2008/0103265 A1 | 5/2008 | Schocker et al. |
| 2008/0167188 A1 | 7/2008 | Fischer et al. |
| 2009/0209661 A1 | 8/2009 | Somerville Roberts et al. |
| 2010/0011610 A1 | 1/2010 | Bittorf et al. |
| 2010/0028451 A1 | 2/2010 | Kaplan et al. |
| 2011/0052680 A1 | 3/2011 | Hendrickson et al. |
| 2011/0268778 A1 | 11/2011 | Dihora et al. |
| 2011/0268802 A1 | 11/2011 | Dihora et al. |
| 2012/0128752 A1 | 5/2012 | Loo et al. |
| 2013/0004617 A1 | 1/2013 | Zhang et al. |
| 2013/0022654 A1 | 1/2013 | Deshmukh et al. |
| 2013/0084379 A1 | 4/2013 | Gregson et al. |
| 2013/0239429 A1 | 9/2013 | Vella et al. |
| 2014/0199244 A1 | 7/2014 | Rijcken et al. |
| 2014/0335032 A1 | 11/2014 | Panandiker et al. |
| 2015/0079139 A1 | 3/2015 | Takehana |
| 2015/0252312 A1 | 9/2015 | De Villeneuve et al. |
| 2016/0038428 A1 | 2/2016 | Harel et al. |
| 2016/0128944 A1 | 5/2016 | Chawrai et al. |
| 2016/0158121 A1 | 6/2016 | Lei et al. |
| 2016/0166480 A1 | 6/2016 | Lei et al. |
| 2016/0206561 A1 | 7/2016 | Kohane et al. |
| 2016/0228338 A9 | 8/2016 | Dihora et al. |
| 2017/0165627 A1 | 6/2017 | Duan et al. |
| 2017/0360676 A1* | 12/2017 | Dihora ............... A61K 8/0241 |
| 2018/0015009 A1 | 1/2018 | Soubiran et al. |
| 2018/0042825 A1 | 2/2018 | Lei et al. |
| 2019/0192444 A1 | 6/2019 | Barzilay et al. |
| 2019/0275490 A1 | 9/2019 | Bachawala |
| 2021/0045409 A1 | 2/2021 | Witteveen et al. |
| 2022/0133603 A1 | 5/2022 | Bachawala et al. |
| 2022/0177815 A1* | 6/2022 | Popplewell ........ C11D 17/0039 |
| 2022/0408771 A1 | 12/2022 | Dihora |
| 2023/0060181 A1 | 3/2023 | Dihora et al. |

FOREIGN PATENT DOCUMENTS

| | | |
|---|---|---|
| EP | 0076515 A1 | 4/1983 |
| EP | 0361677 B2 | 11/1993 |
| EP | 0815743 A2 | 1/1998 |
| EP | 1371410 A1 | 12/2003 |
| EP | 1797946 A2 | 6/2007 |
| RU | 2351364 C2 | 4/2009 |
| WO | 9901214 A1 | 1/1999 |
| WO | 0105926 A1 | 1/2001 |
| WO | 03013538 A1 | 2/2003 |
| WO | 2004064971 A2 | 8/2004 |
| WO | 2006024411 A2 | 3/2006 |
| WO | WO 2006024411 A2 | 3/2006 |
| WO | 2007135583 A2 | 11/2007 |
| WO | 2008118133 A2 | 10/2008 |
| WO | 2009098226 A1 | 8/2009 |
| WO | WO 2009098226 A1 | 8/2009 |
| WO | 2011041395 A2 | 4/2011 |
| WO | 2015091877 A1 | 6/2015 |
| WO | 2016071151 A1 | 5/2016 |
| WO | 2017023830 A1 | 2/2017 |
| WO | 2020195132 A1 | 10/2020 |
| WO | WO 2020195132 A1 | 10/2020 |

OTHER PUBLICATIONS

Leung et al. (2017). Enteric coating of micron-size drug particles through a Würster fluid-bed process. Powder Technology, 317, 247-252.

Luo et al. (2014). Zein-based micro-and nano-particles for drug and nutrient delivery: A review. Journal of Applied Polymer Science, 131(16): 40696, 1-12.

Silverajah et al. (2012). Mechanical, thermal and morphological properties of poly (lactic acid)/epoxidized palm plein blend. Molecules, 17(10), 11729-11747.

Tmakova et al. (2015). Plant-derived surfactants as an alternative to synthetic surfactants: surface and antioxidant activities. Chemical Papers, 70(2), 188-196.

Werner et al. (2007). Air-suspension particle coating in the food industry: Part I—State of the art. Powder Technology, 171(1), 25-33.

English language abstract for WO 2009098226 A1 (2009).

English language abstract for WO 2020195132 A1 (2020).

http://polymerdatabase.com/polymer%20physics/sigma.html downloaded on Apr. 29, 2022.

Ko et al., "Characterization of hydrophilic-hydrophobic polymeric surfaces by contact angle measurements", Journal of Colloid and Interface Science, vol. 82(1) (1981).

OECD 301D method (OECD 1992, Test No. 301 Ready Biodegradability, OECD Guidelines for the Testing of Chemicals, Section 3, OECD Publishing, Paris, https://doi.org/10.1787/9789264070349-en.

Thakore et al. (2001). "Studies on biodegradability, morphology and thermo-mechanical properties of LDPE/modified starch blends." European polymer journal, 37(1), 151-160.

U.S. Appl. No. 16/682,862, filed Nov. 13, 2019.
U.S. Appl. No. 16/830,152, filed Mar. 25, 2020.
U.S. Appl. No. 16/853,003, filed Apr. 20, 2020.
U.S. Appl. No. 17/517,816, filed Nov. 3, 2021.
U.S. Appl. No. 16/776,828, filed Jan. 30, 2020.
U.S. Appl. No. 16/776,965, filed Jan. 30, 2020.
U.S. Appl. No. 16/777,048, filed Jan. 30, 2020.
U.S. Appl. No. 17/724,166, filed Apr. 19, 2022.
U.S. Appl. No. 17/848,345, filed Jun. 23, 2022.
U.S. Appl. No. 17/861,204, filed Jul. 9, 2022.

Jardine. (2022). Amino-functionalized polysaccharide derivatives: Synthesis, properties and application. Current Research in Green and Sustainable Chemistry 5, 100309.

Gasparini et al. (2020). Quantification of residual perfume by Py-GC-MS in fragrance encapsulate polymeric materials intended for biodegradation tests. Molecules, 25, 718.

Larson et al. (2017). Bulky polar additives that greatly reduce the viscosity of concentrated solutions of therapeutic monoclonal antibodies. Journal of Pharmaceutical Sciences, 106, 1211-1217.

Guo et al. (2012). Structure-activity relationship for hydrophobic salts as viscosity-lowering excipients for concentrated solutions of monoclonal antibodies. Pharm Res, 3102-3109.

Kumar et al. (2017). Viscosity-reducing bulky-salt excipients prevent gelation of protein, but not carbohydrate, solutions. Appl Biochem Biotechnol, 1491-1496.

(56) References Cited

OTHER PUBLICATIONS

Wang et al. (2021). Hofmeister effect on the viscosity properties of gelatin in dilute solutions. Colloids and Surfaces B: Biointerfaces, 206, 111944.

* cited by examiner

US 11,878,280 B2

MICROCAPSULES COMPRISING NATURAL MATERIALS

BACKGROUND OF THE INVENTION

1. Field of Invention

This invention relates to controlled release compositions, encapsulation compositions and methods for making and using them.

2. Description of Related Art

There are many microencapsulated delivery systems disclosed in the art to control the release of the encapsulated active, or provide release when a specific trigger is applied. Such systems have previously suffered from a number of drawbacks.

Controlled release microcapsules that provide release of active upon application of shear or friction generally suffer from several drawbacks: (1) such microcapsules are made of highly crosslinked membranes and membrane materials that cannot be broken down by microbes found in the environment, (2) despite such highly crosslinked membranes, the materials of construction of the membrane impart high permeabilities when incorporated into products that contain high levels of surfactant, solvents, and/or water, which results in the premature benefit agent release, (3) they can only effectively encapsulate a limited breadth of benefit agents, (4) they either are so stable that they do not release the benefit agent in use or have insufficient mechanical stability to withstand the processes required to incorporate them in and/or make a consumer product, (5) they do not adequately deposit on the surface that is being treated with consumer product that contains microcapsules, and/or (6) they do not comprise membrane materials that have a favorable environmental degradability profile.

Such microcapsules are made via chemical processes that require the development of a membrane at the oil-water interface. Said membrane can be developed from the oil side or the water side, or both. An emulsion comprising the active material (dispersed phase) is stabilized in a continuous phase. In one mode, a shell material is deposited from the continuous phase onto a dispersed phase via precipitation of the shell material. In another mode, the shell material is manufactured within the dispersed phase, and migration of the shell material is induced via an interfacial reaction or insolubility of the shell material in the oil phase. The two approaches could be combined to develop "multi-shell" capsules.

There is a challenge in designing a membrane that minimizes the diffusion of the encapsulated active into the surrounding formulation, and yet is environmentally biodegradable. Environmentally biodegradable polymers generally swell in water, or are soluble in water. In contrast, microcapsule membranes generally need to resist swelling or dissolution in aqueous cleaning product formulation. A high degree of crosslinking within the membrane can reduce swelling and solubility; however, such highly crosslinked membranes are difficult for environmentally available microbes to digest and breakdown.

A study on biodegradability of LDPE/starch blend by Thakore et. al. [European Polymer Journal 37 (2001) 151-160] shows that a physical mixture that comprises 20% of a natural material that has 100% environmental biodegradability is combined with 80 wt. % of a material 0% biodegradability, wherein there is no chemical reaction taking place between the components, one would expect that the final material would have 20% biodegradability. However, the results explicitly point out that the biodegradability is reduced to 10%. The biodegradability of a membrane is not only dependent on the components that make up the membrane, but how these components are interacting with one another (reaction vs. physical mixture), and the accessibility of the materials to the microbes that will digest these materials.

In WO2020195132A1, Fujifilm clarifies that when isocyanates dissolved in the core material are reacted with highly biodegradable resins in the water phase (e.g. gelatin, chitosan, celluloses), the resulting interfacial membrane shows an increase in biodegradability; however, it is nowhere close to the biodegradability of the biodegradable resin. The inventors also show that an increase in crosslink density is necessary to minimize the diffusion of the core material through the membrane. Such increase in crosslink density reduces the environmental biodegradability of the membrane.

Like WO2020195132A1, art that discusses polyurea capsules, made via the reaction of polyisocyanates with amines, discloses polyisocyanates dissolved in an oil phase, and the amines dissolved in the water phase. These two materials come together at the oil/water interface to produce a polyurea reaction product. However, the polyurea membrane has less than 30% environmental biodegradability.

Surprisingly, incorporating uniquely modified amine moiety containing materials during microcapsule making enables the conjugation of natural materials into the membrane. Such membranes provide better barrier properties to the membrane to reduce the premature leakage of encapsulated hydrophobic active materials, whilst providing higher environmental biodegradability.

While others have attempted to improve the barrier properties of microcapsules, there remains significant shortcoming and limitations in the art. For example, U.S. Pat. No. 9,944,886B2 Hitchcock et. al. describes metal coated microcapsules with improved barrier properties. The Hitchcock metal coating is developed after the formation of the microcapsule membrane, via the use of sterically stabilized nano-suspension of metal particle. Such metal coated microcapsules could improve barrier properties; however, it is difficult to imagine how the encapsulated active would be released, since a metal coating would be difficult to fracture. Furthermore, the processing steps involved to achieve the metal coating are laborious and expensive. Moreover, such metal coating could render the microcapsules non-environmentally biodegradable.

US2011/0268778A1 Dihora et. al. provides microcapsules made using UV initiation in order to form membranes at lower temperatures. However, prior to the free radical polymerization to form the membrane, the hydrophobic active material needs to be heated to temperatures beyond 60° C. Moreover, Example 2 of the application clearly delineates poorer barrier properties of the membrane made via UV initiator versus the same capsules made via use of thermal initiation. Because of the non-transparency of the system, UV initiation to form a membrane has low efficiency. The resulting barrier properties and biodegradability of the resulting polyacrylate microcapsules are poor.

U.S. Pat. No. 9,937,477B2 Zhang et. al. discloses core/shell microcapsules that are manufacture using free radical polymerization of acrylates; such microcapsules require multi-step reactions that require heating the capsules to 95°

C. for up to 6 hours. It is well known that such polyacrylate capsules that are highly crosslinked have poor environmental biodegradability.

Various methods of producing silk fibroin particles are known in the art. In some embodiments, the silk particles can be produced by a polyvinyl alcohol (PVA) phase separation method as described in, e.g., WO 2011/041395. Other methods for producing silk fibroin particles are described, for example, in US 2010/0028451 and WO 2008/118133 (using oil as a template for making silk microspheres or nanospheres), and in Wenk, et al. (2008) J. Control. Release 132:26-34 (using spraying method to produce silk microspheres or nanospheres). However, none of these methods modify the zwitterionic nature of the protein to make it reactive such that it can be incorporated into the membrane of a microcapsule Conventional controlled release particles that comprise a core and a shell have several limitations. First, such capsules prematurely release the active material when suspended in a finished product formulations, such as cleaning product formulations. Second, such capsules have poor environmental biodegradability due to the nature of materials used and the degree of crosslinking that is achieved in order to reduce the diffusion of the active. Third, it is difficult to control the release profile of the encapsulated active. Fourth, poor adhesion of particles to the substrate result in significant loss of the particles, especially when formulations containing such particles are used in rinse-off applications. Examples of such applications include laundering fabrics, shampooing hair, conditioning hair, cleansing the skin, showering, and the like. In such applications, a composition comprising microcapsules is applied to a substrate to initiate cleaning, and subsequently the composition is removed by using water.

Accordingly, it is desired to remove soil and dirt, but desired to retain active materials during the rinsing process by the retention of microcapsules on the substrate.

It is further desired to provide a means to manipulate the release profile of the encapsulated active.

It is further desired to provide microcapsules that are processed at temperatures at or below 60° C., and able to achieve a degree of crosslinking that is sufficient to reduce the diffusion of the encapsulated active out of the microcapsule yet provide more than 50% environmental biodegradability of the membrane material.

Hence, it is desired to provide low permeability microcapsules that are able to retain the encapsulated active in surfactant containing solutions, or under highly dilute aqueous conditions. It is desired to improve the adhesion of microcapsules onto the desired substrate during rinse-off applications. It is desired to release the encapsulated active in larger quantities, and over a longer duration of time. It is desired to have capsules that have a favorable environmental biodegradability profile as defined by OECD 301D method (OECD 1992, Test No. 301 Ready Biodegradability, OECD Guidelines for the Testing of Chemicals, Section 3, OECD Publishing, Paris, https://doi.org/10.1787/9789264070349-en).

All references cited herein are incorporated herein by reference in their entireties. The citation of any reference is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

BRIEF SUMMARY OF THE INVENTION

The present invention relates to microcapsules comprising a core and shell, wherein the shell comprises a membrane developed around the core material to reduce the diffusion of core material into the environment. Materials and methods are presented to seal the pores in the membrane while also improving environmental biodegradability.

The inventors have surprisingly found that incorporation of biodegradable resins in the core material during capsule making achieves a membrane with better barrier properties and better environmental biodegradability. The inventors have discovered that such biodegradable resins need to be modified prior to incorporation into the core, such modifications make them reactive. In the absence of such modification, the biodegradable resins are simply dispersed in the core material, but do not become a part of the membrane surrounding the core material. It is only when these modified resins become a part of the membrane that they impart better barrier properties and better environmental biodegradability.

Accordingly, a first aspect of the invention relates to a method for preparing a composition comprising controlled release particles. The method comprises the sequential steps of:
(a) preparing an oil phase, wherein the oil phase comprises:
  (i) at least one hydrophobic active ingredient, at least one isocyanate, at least one epoxy, at least one organofunctional silane, and optionally a plasticizer; or
  (ii) at least one hydrophobic active ingredient, at least one isocyanate, at least one epoxy, at least one organofunctional silane, at least one pre-reacted natural material resin, and optionally a plasticizer;
(b) preparing an aqueous phase comprising an emulsifier;
(c) combining the oil phase and the aqueous phase to emulsify the at least one hydrophobic active ingredient to provide an aqueous suspension of the at least one hydrophobic active ingredient;
(d) adding to the aqueous suspension at least one amine moiety containing material to react with the at least one isocyanate, the at least one epoxy, or the at least one organofunctional silane to provide a barrier;
(e) heating the aqueous suspension;
(f) adding a natural material to the aqueous suspension to provide a microcapsule having hydroxyl moieties or amine moieties on a surface thereof;
(g) adding an aldehyde to the aqueous suspension to react with the hydroxyl moieties or amine moieties on the surface of the microcapsule; and
(h) adding structuring agents to the aqueous suspension to provide the controlled release particles homogeneously suspended in an aqueous dispersion.

In certain embodiments, the emulsifier is a member selected from the group consisting of polyalkylene glycol ether; polyvinyl acetate; copolymers of polyvinyl acetate; polyacrylamide; poly(N-isopropylacrylamide); poly (2-hydroxypropyl methacrylate); poly(2-ethyl-2-oxazoline); poly (2-isopropenyl-2-oxazoline-co-methyl methacrylate); poly (methyl vinyl ether); polyvinyl pyrrolidone; copolymers of polyvinyl pyrrolidone; 1H-Imidazolium, 1-ethenyl-3-methyl-, chloride; polymer with 1-ethenyl-2-pyrrolidinone; vinyl acetate; colloidal silica; palmitamidopropyltrimonium chloride; distearyl dimonium chloride; cetyltrimethylammonium chloride; quaternary ammonium compounds; aliphatic ammonium halides; alkyldimethyl benzylammonium halides; alkyldimethylethylammonium halides; poly(2-dimethylamino)ethyl methacrylate)methyl chloride quaternary salt; poly(1-vinylpyrrolidone-co-2-dimethylaminoethyl methacrylate); poly(acrylamide-co-diallyldimethylammonium chloride); and polybis(2-chloroethyl)ether-alt-1,3-bis (3-(dimethylamino)propylurea quaternized.

In certain embodiments, step (d) is conducted for 0.5 to 2 hours at room temperature, step (e) comprises increasing a temperature of the aqueous suspension to 35° C., reacting for 1 to 3 hours, then increasing the temperature to 60° C. and reacting for 3 to 6 hours.

In certain embodiments, the at least one amine moiety containing material is at least one member selected from the group consisting of linear aliphatic amines, aromatic amines, silicone amines, branched amines, polypeptides, polyamines, polyetheramines, and amino acids.

In certain embodiments, the at least one isocyanate is at least one member selected from the group consisting of aliphatic isocyanates, aromatic isocyanates, polymeric isocyanates, cyclic isocyanates, hydrophilic isocyanates, hydrophobic isocyanates, isocyanurates, waterborne isocyanates and urethane acrylates containing isocyanate functionalities.

In certain embodiments, the at least one organofunctional silane is at least one member selected from the group consisting of alkoxylated silane, trialkoxy silanes, functionalized trialkoxysilanes, tetraalkoxylated silanes and 1,2-bis(triethyxysilyl)ethane.

In certain embodiments, the at least one epoxy is at least one member selected from the group consisting of epoxidized unsaturated oils, epoxidized alcohols and epoxidized polysaccharides.

In certain embodiments, the natural material comprises a member selected from the group consisting of polypeptide, protein, polysaccharide, oligosaccharide, cellulose, polyphenol and lipid.

In certain embodiments, the aldehyde comprises a member selected from the group consisting of aliphatic dialdehydes, aromatic dialdehydes, cyclic dialdehydes, and polyaldehydes.

In certain embodiments, the at least one pre-reacted natural material resin is included in the oil phase and is a spray dried composite of a polyamide epichlorohydrin and an additional natural material, said spray dried composite formed by curing a spray dried particle at elevated temperature to crosslink the polyamide epichlorohydrin material with amine, hydroxyl, carboxyl, and/or thiol functionalities of at least one of monosaccharides, oligosaccharides, polysaccharides, amino acids, proteins, celluloses, carboxy modified saccharides, celluloses, and mixtures thereof.

In certain embodiments, the at least one pre-reacted natural material resin comprises a polymer having a weight ratio of the polyamide epichlorohydrin to the additional natural material of 1:99.

In certain embodiments, the plasticizer is included in the oil phase and is at least one member selected from the group consisting of methyl esters of rosin, polyazelate esters, di-fatty acid esters, citrate esters, polyadipate esters and polyester resins consisting of inner and intra-esters of polyhydroxy carboxylic acids.

In certain embodiments, the plasticizer is polymeric in nature, and has a molecular weight greater than 1000 Daltons.

In certain embodiments, the controlled release particles have a diameter from 0.1 microns to less than 200 microns.

In certain embodiments, the composition is a powdered food product, a fluid food product, a powdered nutritional supplement, a fluid nutritional supplement, a fluid fabric enhancer, a solid fabric enhancer, a fluid shampoo, a solid shampoo, a hair conditioner, a body wash, a solid antiperspirant, a fluid antiperspirant, a solid deodorant, a fluid deodorant, a fluid detergent, a solid detergent, a fluid hard surface cleaner, a solid hard surface cleaner, a fluid fabric refresher spray, a diaper, an air freshening product, a nutraceutical supplement, a controlled release fertilizer, a controlled release insecticide, a controlled release dye or a unit dose detergent comprising a detergent and the controlled release particles in a water soluble film.

In certain embodiments, at least one suspension agent is included in the composition to suspend the controlled release particles, wherein the at least one suspension agent is at least one member selected from the group consisting of a rheology modifier, a structurant and a thickener.

In certain embodiments, the at least one suspension agent has a high shear viscosity, at 20 $sec^{-1}$ shear rate and at 21° C., of from 1 to 7000 cps and a low shear viscosity, at 0.5 $sec^{-1}$ shear rate and at 21° C., of greater than 1000 cps.

In certain embodiments, the at least one suspension agent is a fluid having a high shear viscosity, at 20 $sec^{-1}$ shear rate and at 21° C., of from 50 to 3000 cps and a low shear viscosity, at 0.5 $sec^{-1}$ shear rate and at 21° C., of greater than 1000 cps.

In certain embodiments, the at least one suspension agent is a member selected from the group consisting of polyacrylates, polymethacrylates, polycarboxylates, pectin, alginate, gum arabic, carrageenan, gellan gum, xanthan gum, guar gum, gellan gum, hydroxyl-containing fatty acids, hydroxyl-containing fatty esters, hydroxyl-containing fatty waxes, castor oil, castor oil derivatives, hydrogenated castor oil derivatives, hydrogenated castor wax, perfume oil, and mixtures thereof.

In certain embodiments, the composition comprises two different controlled release particles which are friction-triggered release microcapsules which release the at least one hydrophobic active ingredient at different rates due to a difference in shell material friability or core material viscosity.

In certain embodiments, the at least one hydrophobic active ingredient comprises a mixture of a hydrophobic active and a material selected from the group consisting of brominated oils, epoxidized oils, highly nonpolar oils, hydrophobically modified inorganic particles, nonionic emulsifiers and oil thickening agents.

In certain embodiments, the composition has an Environmental Biodegradability greater than 50%.

In certain embodiments, the at least one pre-reacted natural material resin is included in the oil phase and is a bulk reaction product of an epoxy or epoxide curing agent and an additional natural material, said composite formed by reacting the epoxy or epoxide curing agent with the additional natural material in a reactor at elevated temperature to crosslink the epoxy or epoxide curing agent with an amine functionality or an acid functionality of the additional natural material, which comprises at least one of amino acids, proteins, carboxy modified saccharides, and mixtures thereof.

In certain embodiments, the at least one pre-reacted natural material resin comprises a polymer having a weight ratio of the epoxy or epoxide curing agent to the additional natural material of 1:99.

A second aspect of the invention is a composition comprising controlled release particles prepared by the inventive method.

In certain embodiments of the composition, at least one of the controlled release particles of the composition comprises:
(A) a core comprising the at least one hydrophobic active ingredient; and
(B) a shell at least partially surrounding the core and comprising a copolymer of a first monomer, a second monomer, and a polymer, wherein:
  (i) the first monomer is at least one member selected from the group consisting of the at least one epoxy, the at least one isocyanate and the at least one organofunctional silane;
  (ii) the second monomer is at least one member selected from the group consisting of an amine and the at least one pre-reacted natural material resin; and
  (iii) the polymer is at least one member selected from the group consisting of a natural polysaccharide, a polypeptide and a plasticizer.

In certain embodiments of the composition, at least one of the controlled release particles of the composition comprises:
(A) a core comprising the at least one hydrophobic active ingredient; and
(B) a shell at least partially surrounding the core and comprising a copolymer of a first monomer, a second monomer, and a polymer, wherein:
  (i) the first monomer is at least one member selected from the group consisting of the at least one epoxy, the at least one isocyanate, a pre-reaction product of polyisocyanate and maleic anhydride;
  (ii) the second monomer is at least one member selected from the group consisting of an amine, a basified biodegradable resin and the at least one pre-reacted natural material resin; and
  (iii) the polymer is at least one member selected from the group consisting of a natural polysaccharide, a polypeptide, a plasticizer and an inorganic solid particle.

In certain embodiments of the composition, the shell is degradable by microbes found in wastewater streams to release the at least one hydrophobic active ingredient.

In certain embodiments of the composition, the at least one hydrophobic active ingredient is at least one member selected from the group consisting of a flavorant, a fragrance, a chromogen, a dye, an essential oil, a sweetener, an oil, a pigment, an active pharmaceutical ingredient, a moldicide, a herbicide, a fertilizer, a phase change material, an adhesive, a vitamin oil, a vegetable oil, a triglyceride and a hydrocarbon.

DETAILED DESCRIPTION OF PREFERRED EMBODIMENTS OF THE INVENTION

Glossary

Throughout the description, where compositions are described as having, including, or comprising specific components, or where processes are described as having, including, or comprising specific process steps, it is contemplated that compositions of the present teachings also consist essentially of, or consist of, the recited components, and that the processes of the present teachings also consist essentially of, or consist of, the recited processing steps.

In the application, where an element or component is said to be included in and/or selected from a list of recited elements or components, it should be understood that the element or component can be any one of the recited elements or components and can be selected from the group consisting of two or more of the recited elements or components.

The use of the singular herein includes the plural (and vice versa) unless specifically stated otherwise. In addition, where the use of the term "about" is before a quantitative value, the present teachings also include the specific quantitative value itself, unless specifically stated otherwise.

It should be understood that the order of steps or order for performing certain actions is immaterial so long as the present teachings remain operable. Moreover, two or more steps or actions can be conducted simultaneously.

As used herein, unless otherwise noted, the terms "capsule", "microcapsule" and "particle" are synonyms, which refer to containers for selectively retaining an active ingredient.

As used herein, unless otherwise noted, the terms "shell," "membrane" and "wall" are synonyms, which refer to barriers at least partially surrounding the core of the particles of the invention.

As used herein, microcapsules "formed under acidic conditions" means that part of the process of forming the microcapsule involves a step where the pH of the suspension in which the microcapsules form is adjusted into the acidic region (less than 7).

As used herein, microcapsules "formed under basic conditions" means that part of the process of forming the microcapsule involves a step where the pH of the suspension in which the microcapsules form is adjusted into the alkaline region (greater than 7).

As used herein, "an unreacted amount" refers to the amount of a reactant not used up in one or more reaction. "An unreacted amount" can be zero to any amount depending on the amount of reactants added.

As used herein, unless otherwise noted, "alkyl" whether used alone or as part of a substituent group refers to straight and branched carbon chains having 1 to 20 carbon atoms or any number within this range, for example, 1 to 6 carbon atoms or 1 to 4 carbon atoms. Designated numbers of carbon atoms (e.g. $C_{1-6}$) shall refer independently to the number of carbon atoms in an alkyl moiety or to the alkyl portion of a larger alkyl-containing substituent. Non-limiting examples of alkyl groups include methyl, ethyl, n-propyl, iso-propyl, n-butyl, sec-butyl, iso-butyl, tert-butyl, and the like. Alkyl groups can be optionally substituted. Non-limiting examples of substituted alkyl groups include hydroxymethyl, chloromethyl, trifluoromethyl, aminomethyl, 1-chloroethyl, 2-hydroxyethyl, 1,2-difluoroethyl, 3-carboxypropyl, and the like. In substituent groups with multiple alkyl groups, the alkyl groups may be the same or different.

The term "substituted" is defined herein as a moiety, whether acyclic or cyclic, which has one or more hydrogen atoms replaced by a substituent or several (e.g., 1 to 10) substituents as defined herein below. The substituents are capable of replacing one or two hydrogen atoms of a single moiety at a time. In addition, these substituents can replace two hydrogen atoms on two adjacent carbons to form said substituent, new moiety or unit. For example, a substituted unit that requires a single hydrogen atom replacement includes halogen, hydroxyl, and the like. A two hydrogen atom replacement includes carbonyl, oximino, and the like. A two hydrogen atom replacement from adjacent carbon atoms includes epoxy, and the like.

The dimensions and values disclosed herein are not to be understood as being strictly limited to the exact numerical values recited. Instead, unless otherwise specified, each such dimension is intended to mean both the recited value and functionally equivalent range surrounding that value. For example, a dimension disclosed as "40 mm" is intended to mean "about 40 mm".

As used herein "cleaning and/or treatment compositions" means products comprising fluid laundry detergents, fabric enhancers, laundry and/or rinse additives, fluid dishwashing detergents, fluid hard surface cleaning and/or treatment compositions, fluid toilet bowl cleaners that may or may not be contained in a unit dose delivery product all for consumer, agricultural, industrial or institutional use.

The term "absorbent article" is used herein in a very broad sense including any article able to receive and/or absorb and/or contain and/or retain fluids and/or exudates, especially bodily fluids/bodily exudates. Exemplary absorbent articles in the context of the present invention are disposable absorbent articles.

The term "disposable" is used herein to describe articles, which are not intended to be laundered or otherwise restored or reused as an article (i.e. they are intended to be discarded after a single use and preferably to be recycled, composted or otherwise disposed of in an environmentally compatible manner). Typical disposable absorbent articles according to the present invention are diapers, surgical and wound dressings, breast and perspiration pads, incontinence pads and pants, bed pads as well as absorbent articles for feminine hygiene like sanitary napkins, panty liners, tampons, interlabial devices or the like. Absorbent articles suitable for use in the present invention include any type of structures, from a single absorbent layer to more complex multi-layer structures. Certain absorbent articles include a fluid pervious topsheet, a backsheet, which may be fluid impervious and/or may be water vapor and/or gas pervious, and an absorbent element comprised there between, often also referred to as "absorbent core" or simply "core".

The term "Sanitary tissue product" or "tissue product" as used herein means a wiping implement for post-urinary and/or post-bowel movement cleaning (toilet tissue products), for otorhinolaryngological discharges (facial tissue products) and/or multi-functional absorbent and cleaning uses (absorbent towels such as paper towel products and/or wipe products). The sanitary tissue products of the present invention may comprise one or more fibrous structures and/or finished fibrous structures, traditionally, but not necessarily, comprising cellulose fibers.

The term "tissue-towel paper product" refers to products comprising paper tissue or paper towel technology in general, including, but not limited to, conventional felt-pressed or conventional wet-pressed tissue paper, pattern densified tissue paper, starch substrates, and high bulk, uncompacted tissue paper. Non-limiting examples of tissue-towel paper products include towels, facial tissue, bath tissue, table napkins, and the like.

"Personal care composition" refers to compositions intended for topical application to skin or hair and can be, for example, in the form of a liquid, semi-liquid cream, lotion, gel, or solid. Examples of personal care compositions can include, but are not limited to, bar soaps, shampoos, conditioning shampoos, body washes, moisturizing body washes, shower gels, skin cleansers, cleansing milks, in-shower body moisturizers, pet shampoos, shaving preparations, etc.

"Bar soap" refers to compositions intended for topical application to a surface such as skin or hair to remove, for example, dirt, oil, and the like. The bar soaps can be rinse-off formulations, in which the product is applied topically to the skin or hair and then subsequently rinsed within minutes from the skin or hair with water. The product could also be wiped off using a substrate. Bar soaps can be in the form of a solid (e.g., non-flowing) bar soap intended for topical application to skin. The bar soap can also be in the form of a soft solid which is compliant to the body. The bar soap additionally can be wrapped in a substrate which remains on the bar during use.

"Rinse-off" means the intended product usage includes application to skin and/or hair followed by rinsing and/or wiping the product from the skin and/or hair within a few seconds to minutes of the application step.

"Ambient" refers to surrounding conditions at about one atmosphere of pressure, 50% relative humidity and about 25° C.

"Anhydrous" refers to compositions and/or components which are substantially free of added or free water.

"Antiperspirant composition" refers to antiperspirant compositions, deodorant compositions, and the like. For example, antiperspirant creams, gels, soft solid sticks, body sprays, and aerosols.

"Soft solid" refers to a composition with a static yield stress of about 200 Pa to about 1,300 Pa. The term "solid" includes granular, powder, bar and tablet product forms.

The term "fluid" includes liquid, gel, paste and gas product forms.

The term "situs" includes paper products, fabrics, garments, hard surfaces, hair and skin.

The term "substantially free of" refers to 2% or less of a stated ingredient. "Free of" refers to no detectable amount of the stated ingredient or thing.

As used herein, the terms "a" and "an" mean "at least one".

As used herein, the terms "include", "includes" and "including" are meant to be non-limiting.

Unless otherwise noted, in discussing the commercial applications below, all component or composition levels are in reference to the active portion of that component or composition, and are exclusive of impurities, for example, residual solvents or byproducts, which may be present in commercially available sources of such components or compositions.

Similarly, all percentages and ratios are calculated by weight unless otherwise indicated and are calculated based on the total composition unless otherwise indicated.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Advantages of the Invention

One or more of the following benefits are provided by preferred embodiments of the invention.

The inventive particles' shell material have an environmental biodegradability greater than 50% as measured by the OECD 301D method that utilizes biological oxygen demand as the criteria for measuring degradability. Conventional capsules utilize polymers that may be biodegradable prior to shell formation, but due to the nature of crosslinkers that are used and the chemical structure of the final crosslinked polymer, microbes are no longer able to attach to the polymer or the backbone to sufficiently degrade the shell material. The inventive particles utilize monomers and polymers that retain degradable functional groups even after the crosslinking is complete, such that microbes in the environment are able to digest the shell material.

The inventive particles adhere onto desired substrates via the use of viscoelastic and electrostatic interactions. By adhering large particles as well as small particles during the rinse off application, greater volumes of active material can be delivered with a higher delivery efficiency of the encapsulated active. Conventional capsules are limited to the deposition of small particles, which carry much less volume of active material. Only a fraction of these small microcapsules fracture during use, resulting in significantly lower delivery efficiency of the encapsulated active. Moreover, inventors have discovered formulation approaches to control the level of aggregation of capsules such that a higher quantity of microcapsules can be retained onto the substrate during a rinse-off or filtration process. Such discovery can reduce the quantity of capsules that are lost in the rinse water, and can reduce the environmental impact.

In order to deliver a consumer noticeable benefit, yet deliver that benefit at a low cost, encapsulation is used to isolate a uniquely different fragrance or flavor active from the non-encapsulated fragrance or flavor that is incorporated into the formulation. Acclamation to a flavor or fragrance requires a much higher concentration of the same fragrance or flavor to achieve noticeability. The invention allows one to encapsulate a uniquely different fragrance or flavor to incorporate into the composition, and achieve noticeability at significantly lower concentrations of the encapsulated active. Improvement of retention of capsules onto the fabric during rinse-off processes also has the potential to reduce cost.

Particles

The invention addresses one or more of the prior art deficiencies described above by providing controlled release particles. The particles are particularly well-suited for use in encapsulation of hydrophobic, nonpolar materials.

The particles are preferably used in a consumer product composition, such as, e.g., a cleaning composition, a fabric care composition and/or a personal care composition.

Compositions of the invention preferably comprise at least one of two different types of particles: a first type of particle that has a natural material on the exterior surface of the microcapsule; and a second type of particle that has a natural material on both the interior wall of the capsule as well as the exterior surface of the microcapsule. The first type of particle is preferably provided by a method in which a novel amine moiety containing material is added to a water phase. The second type of particle is enabled by a method in which a pre-reacted natural material is used in an oil phase, and a novel amine moiety containing material is added to a water phase.

The particles preferably comprise a hydrophobic active ingredient surrounded by a wall material that comprises a mixture of several different polymers—a polyurea, a poly (amine alcohol), a silica, a polyamide, a polyester, polypeptide, polysaccharide, a polyphenol, a cellulose, and optionally, a quaternary amine.

The polyurea preferably comprises a reaction product of 1) an isocyanate functionality and 2) an amine functionality. Preferably, the isocyanate functionality is provided by polymeric isocyanates with a molecular weight greater than 300 grams per mole. Preferably, the amine functionality is provided by, for example, acidic amines such as lysine hydrochloride, urea, tryptophan hydrochloride, guanidine hydrochloride, and the like; neutral amines such as aniline, cyanamide, 4-aminobenzoic acid, and the like; and basic amines such as ethylenediamine, diethylenetriamine, guanidine, pentaethylene hexamine, hexamethylenetetramine, tetraethylene pentamine, xylene diamine, phenyl diamine, and quaternary amines such as Girard's reagent; silicone amines such as aminopropylsilsequioxane oligomer, water borne amino alkyl silsequioxane oligomers, trihydroxysilylpropylamine condensate, 3-aminopropyl(diethoxy)methylsilane, [3-(2-aminoethyl)-aminopropyl] methyl-dimethoxysilane, [3-(2-aminoethyl)-aminopropyl]trimethoxysilane. The amine is preferably a mixture of a basic amine, a silicone amine, and optionally an amine modified polysaccharide. Such a mixture undergoes two simultaneous reactions: (1) a reaction with the isocyanate to form a hydrophilic polyurea shell, and (2) a hydrolysis reaction to form a hydrophilic sol-gel hydrogel. Not to be bound by theory, such a composite shell having lipophilic and lipophobic properties provides better leakage stability of the encapsulated active material. Moreover, the hydrolysis reaction results in the presence of hydroxyl functional groups on the microcapsule surface. In certain embodiments, the amine moiety is provided by a spray dried particle comprising casein whose pH is adjusted to 8.0 or higher using sodium carbonate prior to spray drying; spray dried particle comprising gelatin whose pH is adjusted to 8.0 or higher using sodium carbonate prior to spray drying; spray dried chitosan oligosaccharide whose pH is adjusted to 8.0 or higher using sodium carbonate prior to spray drying; spray dried whey protein whose pH is adjusted to 8.0 or higher using sodium carbonate prior to spray drying; spray dried soy protein whose pH is adjusted to 8.0 or higher using sodium carbonate prior to spray drying; spray dried silk fibroin protein whose pH is adjusted to 8.0 or higher using sodium carbonate prior to spray drying; spray dried composite of a polyamide epichlorohydrin and a natural material, said composite formed by curing the spray dried particle at elevated temperature to crosslink amine, hydroxyl, carboxyl, and/or thiol functionality. Natural materials that generally comprise amine, hydroxyl, carboxyl, and/or thiol functionalities are monosaccharides, oligosaccharides, polysaccharides, amino acids, proteins, celluloses, carboxy modified saccharides and celluloses, and the like.

The poly(amine alcohol) preferably comprises a reaction product of 1) an epoxy and 2) an amine functionality. The silica preferably comprises the product of silica hydrolysis.

The biodegradable membrane comprising polysaccharide, polypeptide, polyphenol, or cellulose is achieved via:
1) the reaction of basified biodegradable resin or pre-reacted natural material resin with isocyanate or epoxy; or
2) the reaction of primary or secondary amines on the microcapsule surface with natural materials via the use of an aldehyde linking agent; or
3) the reaction of alcohol groups on the microcapsule surface with natural materials via the use of an aldehyde linking agent.

The quaternary amine is preferably a material that has a primary amine moiety and a quaternary amine moiety. The primary amine moiety can preferably react with isocyanate functionality to form a polyurea layer, and the highly polar quaternary amine functionality interacts with the surrounding aqueous phase. Suitable quaternary amine materials include, for example, Girard's reagent. Other suitable quaternary amines include but are not limited to compounds represented by formulas (1)-(4) below.

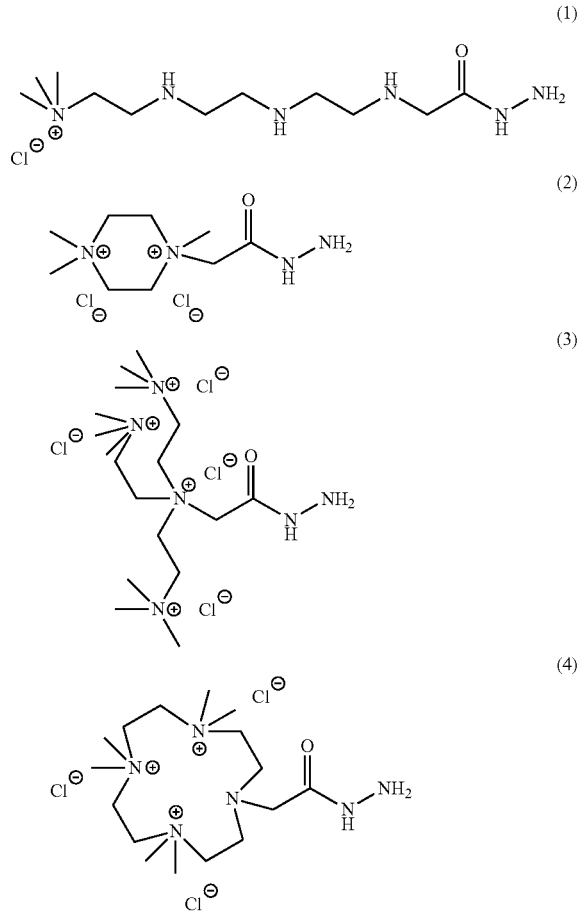

The hydrophobic active ingredient is a hydrophobic substance that is active (or effective) to provide a desired effect, alone or in combination with other substances and/or conditions. It is present in the particles in an amount effective to provide a desired effect. The amount can be, e.g., from 47 wt. % or 59 wt. % or 66 wt. % to 73 wt. % or 78 wt. % or 81 wt. % or 93.5 wt. %, wherein the weight percentages are based on the weight of hydrophobic active divided by the weight of dry matter in the composition.

The hydrophobic active ingredient is preferably a member selected from the group consisting of a flavorant, a fragrance, a chromogen, a dye, an essential oil, a sweetener, an oil, a pigment, an active pharmaceutical ingredient, a moldicide, a herbicide, a fertilizer, a pheromone, phase change material, an adhesive, a vitamin oil, a vegetable oil, a triglyceride and a hydrocarbon.

Suitable flavorants include but are not limited to oils derived from plants and fruits such as citrus oils, fruit essences, peppermint oil, clove oil, oil of wintergreen, anise, lemon oil, apple essence, and the like. Artificial flavoring components are also contemplated. Those skilled in the art will recognize that natural and artificial flavoring agents may be combined in any sensorially acceptable blend. All such flavors and flavor blends are contemplated by this invention. Carriers may also be mixed with flavors to reduce the intensity, or better solubilize the materials. Carriers such as vegetable oils, hydrogenated oils, triethyl citrate, and the like are also contemplated by the invention.

Suitable fragrances include but are not limited to compositions comprising materials having an LogP (logarithm of octanol-water partition coefficient) of from about 2 to about 12, from about 2.5 to about 8, or even from about 2.5 to about 6 and a boiling point of less than about 280° C., from about 50° C. to about less than about 280° C., from about 50° C. to about less than about 265° C., or even from about 80° C. to about less than about 250° C.; and optionally, an ODT (odor detection threshold) of less than about 100 ppb, from about 0.00001 ppb to about less than about 100 ppb, from about 0.00001 ppb to about less than about 50 ppb or even from about 0.00001 ppb to about less than about 20 ppb. Diluents that are miscible in the fragrance oil, and act to reduce the volatility of the fragrance oil, such as isopropyl myristate, iso E super, triethyl citrate, vegetable oils, hydrogenated oils, neobee, and the like are also contemplated by the invention.

Suitable chromogens include but are not limited to Michler's hydrol, i.e. bis(p-dimethylaminophenyl)methanol, its ethers, for example the methyl ether of Michler's hydrol and the benzylether of Michler's hydrol, aromatic sulfonic and sulfinic esters of Michler's hydrol, for example the p-toluenesulfinate of Michler's hydrol, and derivatives of bis(p-dimethylaminophenyl)methylamine, e.g., N[bis(p-dimethylaminophenyl)methyl]morpholine.

Suitable dyes include but are not limited to Sudan Red 380, Sudan Blue 670, Baso Red 546, Baso Blue 688, Sudan Yellow 150, Baso Blue 645, Flexo Yellow 110, and Flexo Blue 630, all commercially available from BASF; Oil Red 235, commercially available from Passaic Color and Chemical; Morfast Yellow 101, commercially available from Morton; Nitro Fast Yellow B, commercially available from Sandoz; Macrolex Yellow 6G, commercially available from Mobay. Preferred dyes are those having good solubility in aromatic solvents.

Suitable essential oils include but are not limited to those obtained from thyme, lemongrass, citrus, anise, clove, aniseed, roses, lavender, citronella, eucalyptus, peppermint, camphor, sandalwood, cinnamon leaf and cedar. Essential oils that exhibit antimicrobial properties are also contemplated by this invention.

Suitable sweeteners include but are not limited to materials that contain varying amounts of disaccharide and/or fructose; erythritol, honey, and/or evaporated cane juice; and rebaudioside A, and the like.

Suitable pigments include but are not limited to pearl pigments of mica group such as titanium dioxide-coated mica and colored titanium dioxide-coated mica; and pearl pigments of bismuth oxychlorides such as colored bismuth oxychloride. Such pigments are available on the market under various trade names: Flamenco series (by the Mearl Corporation), TIMIRON COLORS (by MERCK) as titanium dioxide-coated mica, Timica Luster Pigments (by MEARL). Cloisonee series (by MEARL), COLORON series (by MERCK), SPECTRA-PEARL PIGMENTS (by Mallinckrodt) as colored titanium dioxide-coated mica and MIBIRON COLORS series (by MERCK) as colored bismuth oxychloride.

Suitable active pharmaceutical ingredients include but are not limited to water insoluble materials that have a melting point below 50° C.

Suitable moldicides include but are not limited to an inorganic biocide selected from the group consisting of a metal, a metal compound and combinations thereof. Preferably, the inorganic biocide is copper, cobalt, boron, cadmium, nickel, tin, silver, zinc, lead bismuth, chromium and arsenic and compounds thereof. More preferably, the copper compound is selected from the group consisting of copper hydroxide, cupric oxide, cuprous oxide, copper carbonate, basic copper carbonate, copper oxychloride, copper 8-hydroxyquinolate, copper dimethyldithiocarbamate, copper omadine and copper borate. Suitable moldicides further include but are not limited to fungicidal compounds such as, e.g., isothiazolone compounds. Typical examples of isothiazolone compounds include but not limited to: methylisothiazolinone; 5-chloro-2-methyl-4-isothiazoline-3-one, 2-methyl-4-isothiazoline-3-one, 2-n-octyl-4-isothiazoline-3-one, 4,5-dichloro-2-n-octyl-4-isothiazoline-3-one, 2-ethyl-4-isothiazoline-3-one, 4,5-dichloro-2-cyclohexyl-4-isothiazoline-3-one, 5-chloro-2-ethyl-4-isothiazoline-3-one, 2-octyl-3-isothiazolone, 5-chloro-2-t-octyl-4-isothiazoline-3-one, 1,2-benzisothiazoline-3-one, preferably 5-chloro-2-methyl-4-isothiazoline-3-one, 2-methyl-4-isothiazoline-3-one, 2-n-octyl-4-isothiazoline-3-one, 4,5-dichloro-2-n-octyl-4-isothiazoline-3-one, 1,2-benzisothiazoline-3-one, etc., more preferably 5-chloro-2-methyl-4-isothiazoline-3-one, 2-n-octyl-4-isothiazoline-3-one, 4,5-dichloro-2-n-octyl-4-isothiazoline-3-one, 1,2-benzisothiazoline-3-one, chloromethylisothiazolinone, 4,5-Dichloro-2-n-octyl-3 (2H)-isothiazolone and 1,2-benzisothiazolin-3-one.

Suitable herbicides include but are not limited to 2-(2-chloro-4-methylsulfonylbenzoyl)-1,3-cyclohexanedione, 2-(2-nitrobenzoyl)-4,4-dimethyl-1,3-cyclohexanedione, 2-(2-(nitrobenzoyl)-5,5-dimethyl-1,3-cyclohexanedione, and their 2-benzoylcyclohexanedione derivatives, in addition to those listed in WO2006024411A2.

Suitable phase change materials include but are not limited to a crystalline alkyl hydrocarbon which is comprised of one or more crystalline straight chain alkyl hydrocarbons having 14 or more carbon atoms and heats of fusion greater than 30 cal/g. The melting and freezing point of the alkyl hydrocarbon is in the range of 0° to 80° C., preferably 5° to 50° C., and most preferably, 18° to 33° C. Representative materials are crystalline polyolefins such as polyethylene, polypropylene, polybutene, crystalline polystyrene, crystalline chlorinated polyethylene and poly(4-methylpentene-1). Crystalline ethylene copolymers such as ethylene vinylacetate, crystalline ethylene acrylate copolymers, ionomers, crystalline ethylene-butene-1 copolymers and crystalline ethylene-propylene copolymers are also useful polyolefins. Preferably, the polyolefins are crosslinked such that they are form stable upon heating above their crystalline melting point.

Suitable adhesives include but are not limited to compositions comprising an elastomer and a tackifying agent. The elastomer adds toughness to the adhesive film and also is responsible for at least part of the required initial pressure-sensitive tackiness. The elastomeric materials are water insoluble and are inherently tacky or are capable of being rendered tacky by mixture with compatible tackifying resins. Preferably the elastomers are natural rubber or butadiene or isoprene synthetic polymers or copolymers such as butadiene-isobutylene copolymers, butadiene-acrylonitrile copolymers, butadiene-styrene copolymers, polychloroprene or similar elastomers. A combination of the above elastomers may be utilized. Preferred tackifying agents include unsaturated natural resins such as rosin or derivatives thereof, such as rosin esters of polyols such as glycerol or pentaerythritol, hydrogenated rosins or dehydrogenated rosins Suitable vitamin oils include but are not limited to fat-soluble vitamin-active materials, pro vitamins and pure or substantially pure vitamins, both natural and synthetic, or chemical derivatives thereof, crude extractions containing such substances, vitamin A, vitamin D, and vitamin E active materials as well as vitamin K, carotene and the like, or mixtures of such materials. The oil-soluble vitamin oil concentrate may be a high potency fish liver oil containing vitamin A and/or D, a synthetic vitamin A palmitate and/or acetate concentrated in an oil solution, vitamin D, or D either concentrated in oil solution or as an oleaginous resin, vitamin E (d-alpha tocopheryl acetate) in an oil solution, or vitamin K in oil solution, or beta-carotene as a crystalline oil suspension in oil.

Suitable vegetable oils include but are not limited to oils derived from palm, corn, canola, sunflower, safflower, rapeseed, castor, olive, soybean, coconut and the like in both the unsaturated forms and hydrogenated forms, and mixtures thereof.

Suitable triglycerides include but are not limited to those disclosed in U.S. Pat. No. 6,248,909B1.

Suitable hydrocarbons that can be the active or can be used in combination with the active in order to change the physical or chemical properties of the active, include but are not limited to, waxes, density modifiers, surface tension modifiers, melting point modifiers, viscosity modifiers, and mixtures thereof. Examples include animal waxes such as beeswax, plant waxes such as carnauba wax, candelilla wax, bayberry wax, castor wax, tallow tree wax, soya wax, rice bran wax, hydrogenated rice bran wax, soya wax, hydrogenated soya wax, hydrogenated vegetable oil. Examples of petroleum derived waxes are paraffin waxes and microcrystalline waxes. An example of synthetic wax is polyethylene wax. Examples of materials that can modify the density of the active phase in the particle are brominated vegetable oil, nanoclays such as montmorrilonite or kaolin, hydrophobically modified clays, hydrophobically modified precipitated silicas or fumed silicas. Examples of oil thickening agents are waxes mentioned above, modified organopolysiloxanes, silicone gums, hydrogenated castor oil, paraffin oils, polyolefins, and the like.

The emulsifier is present in the suspension, on a dry basis (weight of emulsifier per weight of dry matter in the suspension), of the invention in an amount effective to achieve the desired particle size distribution. The amount can be, e.g., from about 1.5 wt. % to about 10 wt. % or at least 1.5 wt. %, or at least 5 wt. % or at least 7.4 wt. % or at least 8.2 wt. %, or at least 10 wt. % or not greater than 20 wt. %.

Emulsifiers of all types are suitable for use in the practice of the present process though it is to be appreciated, and those skilled in the art will readily recognize that different systems, e.g., different core monomer and/or core materials, will be better suited with one or more classes of emulsifiers than others. Specifically, while the present teachings are applicable to anionic, cationic, non-ionic and amphoteric emulsifiers generally, preferred emulsifiers are non-ionic emulsifiers, particularly those having polyalkylether units, especially polyethylene oxide units, with degrees of polymerization of the alkylene ether unit of greater than about 6. Preferred emulsifiers are those which significantly reduce the interfacial tension between the continuous water phase and dispersed oil phase composition, and thereby reduce the tendency for droplet coalescence. In this regard, generally the emulsifiers for use in the water phase for aiding in the oil in water emulsion or dispersion will have HLB values of from 11 to 17. Of course, emulsifiers/surfactants of lower and higher HLB values that achieve the same objective as noted are also included.

Exemplary emulsifiers include, but are not limited to gums such as acacia gum, gum arabic, konjac gum, and xantham gum; poly(meth)acrylic acids and derivatives. Most preferably, the emulsifier/emulsion stabilizer is a polyvinyl pyrrolidone, copolymers of polyvinyl pyrrolidone with vinyl acetate, vinyl imidazole; polyglycerol oleates, colloidal silica.

Additional exemplary anionic surfactants and classes of anionic surfactants suitable for use in the practice of the present invention include: sulfonates; sulfates; sulfosuccinates; sarcosinates; alcohol sulfates; alcohol ether sulfates; alkylaryl ether sulfates; alkylaryl sulfonates such as alkylbenzene sulfonates and alkylnaphthalene sulfonates and salts thereof; alkyl sulfonates; mono- or di-phosphate esters of polyalkoxylated alkyl alcohols or alkylphenols; mono- or di-sulfosuccinate esters of C12 to C15 alkanols or polyalkoxylated C12 to C15 alkanols; ether carboxylates, especially alcohol ether carboxylates; phenolic ether carboxylates; polybasic acid esters of ethoxylated polyoxyalkylene glycols consisting of oxybutylene or the residue of tetrahydrofuran; sutfoalkylamides and salts thereof such as N-methyl-N-oleoyltaurate Na salt; polyoxyalkylene alkylphenol carboxylates; polyoxyalkylene alcohol carboxylates alkyl polyglycosidelakenyl succinic anhydride condensation products; alkyl ester sulfates; naphthalene sulfonates; naphthalene formaldehyde condensates; alkyl sulfonamides; sufonated aliphatic polyesters; sulfate esters of styrylphenyl alkoxylates; and sulfonate esters of styrylphenyl alkoxylates and their corresponding sodium, potassium, calcium, magnesium, zinc, ammonium, alkylammonium, diethanolammonium, or triethanolammonium salts; salts of ligninsulfonic acid such as the sodium, potassium, magnesium, calcium or ammonium salt; polyarylphenol polyalkoxyether sulfates and polyarylphenol polyalkoxyether phosphates; and sulfated alkyl phenol ethoxylates and phosphated alkyl phenol ethoxylates; sodium lauryl sulfate; sodium laureth sulfate; ammonium lauryl sulfate; ammonium laureth sulfate; sodium methyl cocoyl taurate; sodium lauroyl sarcosinate; sodium cocoyl sarcosinate; potassium coco hydrolyzed collagen; TEA (triethanolamine) lauryl sulfate; TEA (Triethanolamine) laureth sulfate; lauryl or cocoyl sarcosine; disodium oleamide sulfosuccinate; disodium laureth sulfosuccinate; disodium dioctyl sulfosuccinate; N-methyl-N-oleoyltaurate Na salt; tristyrylphenol sulphate; ethoxylated lignin sulfonate; ethoxylated nonylphenol phosphate ester calcium alkylbenzene sulfonate; ethoxylated tridecylalcohol phosphate ester, dialkyl sulfosuccinates; perfluoro (C6-C18)alkyl phosphonic acids; perfluoro(C6-C18)alkyl-phosphinic acids; perfluoro(C3-C20)alkyl esters of carboxylic acids; alkenyl succinic acid diglucamides; alkenyl succinic acid alkoxylates; sodium dialkyl sulfosuccinates; and alkenyl succinic acid alkylpolyglykosides. Further exemplification of suitable anionic emulsifiers include, but are not limited to, water-soluble salts of alkyl sulfates, alkyl ether sulfates, alkyl isothionates, alkyl carboxylates, alkyl sulfosuccinates, alkyl succinamates, alkyl sulfate salts such as sodium dodecyl sulfate, alkyl sarcosinates, alkyl derivatives of protein hydrolyzates, acyl aspartates, alkyl or alkyl ether or alkylaryl ether phosphate esters, sodium dodecyl sulphate, phospholipids or lecithin, or soaps, sodium, potassium or ammonium stearate, oleate or palmitate, alkylarylsulfonic acid salts such as sodium dodecylbenzenesuifonate, sodium dialkylsulfosuccinates, dioctyl sulfosuccinate, sodium dilaurylsulfosuccinate, poly(styrene sulfonate) sodium salt, alkylene-maleic anhydride copolymers such as isobutylene-maleic anhydride copolymer, or ethylene maleic anhydride copolymer poly(styrene sulfonate), tragacanth gum, almond gum and agar.

Exemplary amphoteric and cationic emulsifiers include alkylpolyglycosides; betaines; sulfobetaines; glycinates; alkanol amides of C8 to C18 fatty acids and C8 to C18 fatty amine polyalkoxylates; C1 to C18 alkyldimethylbenzylammonium chlorides; coconut alkyldimethylaminoacetic acids: phosphate esters of C8 to C18 fatty amine polyalkoxylates; alkylpolyglycosides (APG) obtainable from an acid-catalyzed Fischer reaction of starch or glucose syrups with fatty alcohols, in particular C8 to C18 alcohols, especially the C8 to C10 and C12 to C14 alkylpolyglycosides having a degree of polymerization of 1.3 to 1.6, in particular 1.4 or 1.5. Additional cationic emulsifiers include quaternary ammonium compounds with a long-chain aliphatic radical, e.g. distearyldiammonium chloride, and fatty amines. Among the cationic emulsifiers which may be mentioned are alkyldimethylbenzylammonium halides, alkyldimethylethyl ammonium halides, etc. specific cationic emulsifiers include palmitamidopropyl trimonium chloride, distearyl dimonium chloride, cetyltrimethylammonium chloride, 1H-Imidazolium, 1-ethenyl-3-methyl-, chloride, polymer with 1-ethenyl-2-pyrrolidinone, and polyethyleneimine. Additional amphoteric emulsifiers include alkylaminoalkane carboxylic acids betaines, sulphobetaines, imidazoline derivatives, lauroamphoglycinate, sodium cocoaminopropionate, and the zwitterionic emulsifier cocoamidopropyl betaine.

Suitable non-ionic emulsifiers are fatty acid esters of polyoxyethylene sorbitan; alkoxylated vegetable oils; fatty acid alkoxylates; sorbitan alkoxylates; sorbitol esters; C8 to C22 alkyl or alkenyl polyglycosides; polyalkoxy styrylaryl ethers; amine oxides especially alkylamine oxides; block copolymer ethers; polyalkoxylated fatty glyceride; polyalkylene glycol ethers; linear aliphatic or aromatic polyesters; organo silicones; sorbitol ester alkoxylates; ethoxylated castor oil; amides of fatty acids such as stearamide, lauramide diethanolamide, and lauramide monoethanolamide; aryl ethers of polyoxyalkylene glycols such as polyoxyethylene glycol nonylphenyl ether and polypropylene glycol stearyl ether. Also preferred as non-ionic emulsifiers are various latex materials, stearates, lecithins.

Suitable amines include but are not limited to linear aliphatic amines, aromatic amines, silicone amines, branched amines, polypeptides, polyamines, and amino acids. In preferred embodiments, the amine is a mixture of silane amines, diamines, and amine modified polysaccharides. Generally, amines are listed by their pKa values, and this defines whether the amine is acidic, basic, or neutral. Acidic amines such as lysine hydrochloride, urea, tryptophan hydrochloride, guanidine hydrochloride, and the like; neutral amines such as aniline, cyanamide, 4-aminobenzoic acid, and the like; and basic amines such as ethylenediamine, diethylenetriamine, guanidine, guanidine carbonate. pentaethylene hexamine, hexamethylenetetramine, tetraethylene pentamine, and Girard's reagent; silicone amines such as aminopropylsilsequioxane oligomer, water borne amino alkyl silsequioxane oligomers, trihydroxysilylpropylamine condensate, 3-aminopropyl(diethoxy)methylsilane, [3-(2-aminoethyl)-aminopropyl] methyldimethoxysilae, [3-(2-aminoethyl)-aminopropyl]tri-methoxysilane; guanidine carbonate; amino acids such as Aspartic acid, glutamic acid, lysine, arginine, histidine, glycine, alanine, serine, threonine, tyrosine, asparagine, glutamione, cysteine.

The amine is present in particles of the invention in an amount effective to react with the isocyanate moiety, the organofunctional silane moiety, the epoxy moieties to an extent effective to provide the particles with desired durability. The amount of amine on a dry basis (weight of amine per weight of dry matter in the suspension) can be, e.g., from 0.1 wt. % or 0.7 wt. % or 1.0 wt. % or 1.5 wt. % to 2.0 wt. % or 2.5 wt. % or 3.6 wt. %.

In certain embodiments, the isocyanate comprises aliphatic isocyanates, aromatic isocyanates, polymeric isocyanates, cyclic isocyanates, hydrophilic isocyanates, hydrophobic isocyanates, waterborne isocyanates. Exemplary isocyanates are selected from the group consisting of hexamethylene diisocyanates (Desmodur N3600, Desmodur N3800, Desmodur N3900, Desmodur N3200, Desmodur N3300, Desmodur N3400, Takenate D-170N), isophorone diisocyanates (Desmodur XP2565, Desmodur Z4470), blends of hexamethylene diisocyanate and isophorone diisocyanate (Desmodur XP2847, Desmodur XP2489, Desmodur XP2838, Desmodur XP2763), pentane-1,5-diisocyanate (Stabio D-370N, Stabio D-376N), xylylene diisocyanate (Takenate 500, Takenate 600, Takenate D-110N, Takenate D-131N), polymeric methylene diphenyl diisocyanate (Mondur MR Lite), polymeric MDI (Desmodur VK 5, Desmodur VL R10, Desmodur 44V40L, Desmodur 44V70L), polyether modified hydrophilic polyisocyanates (Bayhydur XP2451/1, Bayhydur XP2547, Bayhydur XP2759, Bayhydur Ultra 304, Bayhydur Ultra 2487/1), CN9302, ionically modified isocyanates (Bayhydur 2858 XP, Bayhydur XP2759, Bayhydur eco 7190), and the like.

In certain embodiments, the organofunctional silane as at least one member selected from the group consisting of alkoxylated silane, trialkoxy silanes, functionalized trialkoxysilanes (amino, glycidoxy, methacryloxy, vinyl), tetraalkoxylated silanes including tetramethoxy silane and tetraethoxy silane, 1,2-bis(triethyxysilyl)ethane.

The organofunctional silane is present in particles of the invention in an amount effective to hydrolyze in water and react with the amine moiety to create Si—O—Si bonds. The amount of amine on a dry basis (weight of organofunctional silane per weight of dry matter in the suspension) can be, e.g., from 0.1 wt. % or 0.7 wt. % or 1.0 wt. % or 1.5 wt. % to 2.0 wt. % or 2.5 wt. % or 3.6 wt. %.

In certain embodiments, the basified biodegradable resin comprises a protein, or polysaccharide, or oligosaccharide, or cellulose, or polyphenol, or lipid. The hydroxyl or amine functionalities of these materials have been made more reactive by altering the pH. Preferably, the pH of the protein, or polysaccharide, or oligosaccharide, or lipid is increased using an organic or inorganic base, preferably sodium carbonate, and the mixture is dehydrated to yield a powder. Nonlimiting examples of basified biodegradable resins include spray dried particle comprising casein whose pH is adjusted to 8.0 or higher using sodium carbonate prior to spray drying; spray dried particle comprising gelatin whose pH is adjusted to 8.0 or higher using sodium carbonate prior to spray drying; spray dried chitosan oligosaccharide whose pH is adjusted to 8.0 or higher using sodium carbonate prior to spray drying; spray dried whey protein whose pH is adjusted to 8.0 or higher using sodium carbonate prior to spray drying; spray dried soy protein whose pH is adjusted to 8.0 or higher using sodium carbonate prior to spray drying; spray dried silk fibroin protein whose pH is adjusted to 8.0 or higher using sodium carbonate prior to spray drying; spray dried lignin whose pH is adjusted to 8.0 or higher using sodium carbonate prior to spray drying; spray dried tannic acid whose pH is adjusted to 8.0 or higher using sodium carbonate prior to spray drying; spray dried carboxymodified cellulose whose pH is adjusted to 8.0 or higher using sodium carbonate prior to spray drying.

Commercially available examples of proteins of use in preparing the basified biodegadable resin comprise proteins including, but are not limited to, unmodified silk protein, zein, gelatin, keratin, collagen and any polypeptide, such as polylysine; hydrolyzed proteins such as COLLASOL (high molecular weight, soluble, marine collagen; Croda), CROPEPTIDE (hydrolyzed wheat protein and hydrolyzed wheat starch; Croda), CROSILK 10000 (hydrolyzed silk protein; Croda), CROTEIN (hydrolyzed collagen; Croda), HYDROLACTIN 2500 (hydrolyzed milk protein; Croda), HYDROSOLANUM (hydrolyzed vegetable protein; Croda), HYDROSOY 2000 PE (hydrolyzed soy protein; Croda), HYDROTRITICUM 2000 PE (hydrolyzed wheat protein; Croda), KERASOL (hydrolyzed keratin; Croda), PROLEVIUM (cottonseed protein hydrolyzate; Croda), PROSINA (hydrolyzed keratin; Croda), TRITISOL (Hydrolyzed wheat protein; Croda), Fision KeraVeg18 (wheat amino acids, soy amino acids; Tri-K), MILK-TEIN (hydrolyzed milk protein; Tri-K), Rice PRO-TEIN (hydrolyzed rice protein; Tri-K), RICE-QUAT C (cocodimonium hydroxypropyl hydrolyzed rice protein; Tri-K), SOY-QUAT L (laurdimonium hydroxypropyl hydrolyzed soy protein; Tri-K), WHEAT-QUAT C (cocodimonium hydroxypropyl hydrolyzed wheat protein; Tri-K), QUINOA PRO EX (hydrolyzed quinoa; Tri-K), BARLA-TEIN Pro (hydrolyzed barley protein; Tri-K), KERA-QUAT WKP (hydrolyzed keratin; Tri-K), KERA-TEIN 1000 (hydrolyzed keratin; Tri-K), KERA-TEIN 1000 SD (hydrolyzed keratin; Tri-K), Proto-lan 8 (cocoyl hydrolyzed collagen; Tri-K), Proto-lan KT (cocoyl hydrolyzed collagen; Tri-K), SILK AA-QUAT C (cocodimonium hydroxypropyl silk amino acids; Tri-K), AMINO SILK SF (silk amino acids; Tri-K), Collagen Hydrolyzate Cosmetic N-55 (Tri-K), FLAX-TEIN Pro (hydrolyzed linseed protein; Tri-K), SOY-TEIN NL (hydrolyzed soy protein; Tri-K), Silk PRO-TEIN (hydrolyzed silk; Tri-K), WHEAT-TEIN W (hydrolyzed wheat protein; Tri-K), and MARI-COLL N-30 (hydrolyzed collagen; Tri-K).

The basified biodegradable resin is present in particles of the invention in an amount effective to react with isocyanate and epoxy moieties. The amount of basified biodegradable resin on a dry basis (weight of basified biodegradable resin per weight of dry matter in the suspension) can be, e.g., from 0.1 wt. % or 0.4 wt. % or 0.6 wt. % or 1.0 wt. % to 1.4 wt. % or 2.0 wt. % or 3.8 wt. %.

In certain embodiments, the inorganic solid particles comprise a member selected from the group consisting of organically modified or water insoluble clays, minerals, salts such as talc, calcium carbonate, bentonite.

The inorganic solid particles are present in particles of the invention in an amount effective to improve the barrier properties of the membrane. The amount of inorganic solid particles on a dry basis (weight of inorganic solid particles per weight of dry matter in the suspension) can be, e.g., from 0.1 wt. % or 0.2 wt. % or 0.3 wt. % or 0.5 wt. % to 0.7 wt. % or 1.0 wt. % or 1.8 wt. %.

In certain embodiments, the protein comprises a member selected from the group consisting of proteinogenic L-amino acids, animal or plant proteins, protein isolates, animal or plant protein hydrolysates, animal or plant proteins produced by physicochemical or fermentative or enzymatic treatment. Animal based proteins are preferably derived from meat (mammals, birds, reptiles, amphibians, fish), crabs, crustaceans, mussels, mollusks, insects, eggs, milk, casein, whey, gelatin, algae and mixtures thereof. Plant based proteins are preferably derived from cereals such as wheat, barley, rye, spelt gluten, rapeseed, sunflower, rice, potato, corn, soybean, bean, pea, chickpea, lentil, lupin, alfalfa, hemp, chitosan, and mixtures thereof.

The proteins are preferably present in particles of the invention in an amount effective to improve the environmental biodegradability of the particles. The amount of protein on a dry basis (weight of protein per weight of dry matter in the suspension) can be, e.g., from 5 wt. % or 10 wt. % or 20 wt. % or 40 wt. % to 60 wt. % or 77 wt. % or 84 wt. %.

In certain embodiments, the polysaccharide comprises a member selected from the group consisting of natural starches such as tapioca, potato, corn, rice, wheat; modified starches such as carboxy modified polysaccharide or cellulose such as carboxymethyl starch, carboxymethyl chitosan, chitosan oligosaccharide, hydroxy propyl methyl starch, hydroxy propyl cellulose, ethyl cellulose, methyl cellulose, and octenyl succinic anhydride modified starch.

The polysaccharides are present in particles of the invention in an amount effective to improve the environmental biodegradability of the particles. The amount of polysaccharides on a dry basis (weight of polysaccharide per weight of dry matter in the suspension) can be, e.g., from 5 wt. % or 10 wt. % or 20 wt. % or 40 wt. % to 60 wt. % or 77 wt. % or 84 wt. %.

In certain embodiments, the pre-reacted natural material resin comprises a monomer or polymer having at least 1 functional group that is capable of reacting with isocyanate or epoxy groups. The pre-reacted natural material resin comprises a natural material and a crosslinker. The natural material is selected from the group consisting of polypeptide or protein, or polysaccharide, or oligosaccharide, or cellulose, or polyphenol, or lipid. The crosslinker is selected from the group consisting of water-based crosslinking resins that are reactive with amine, carboxyl, hydroxyl, and thiol functionality such as epoxy, epoxide curing agent, or polyamide epichlorohydrin. Preferably the crosslinker is polyamide epichlorohydrin that has a high content of secondary amines. In a preferred embodiment, the pre-reacted natural material resin is made by pursuing the following procedure: 1) the natural material is mixed with the polyamide epichlorohydrin to make a homogeneous solution in water; 2) the pH of the system is adjusted to optimize conditions for the reaction; 3) the mixture is dehydrated, preferably using a spray drying process, and 4) the resulting powder is heated at a temperature greater than 100° C. for more than 30 minutes to assure crosslinking. Nonlimiting examples of pre-reacted natural material resin comprise polyamide epichlorohydrin, epoxy, or epoxide curing agent reaction product with proteins such as casein, whey protein, soy protein, silk protein, zein protein, and the like; reaction product with oligosaccharides and polysaccharides such as chitosan oligosaccharide, carboxymethyl starch, alginic acid, hyaluronic acid, pectin, glucuronic acid, gum Arabic, and the like; reaction products with cellloses such as caroxymethyl cellulose, microcrystalline cellulose, hydroxyethyl cellulose, hydroxypropyl methyl cellulose, hydroxypropylmethyl cellulose phthalate, hydroxypropyl methyl cellulose acetate succinate, and the like; reaction products with polyphenols such as lignin, tannic acid, and the like; and mixtures thereof.

The pre-reacted natural material comprises a polyamide epichlorohydrin to natural material weight ratio of 1:99, or 4:96, or 5:95, or 8:92, or 10:90, or 20:80, or 50:50.

The pre-reacted natural material comprises an epoxide curing agent to natural material weight ratio of 1:99, or 4:96, or 5:95, or 8:92, or 10:90, or 20:80, or 50:50.

The pre-reacted natural material is present in particles of the invention in an amount effective to improve the barrier properties and environmental biodegradability of the membrane. The amount of pre-reacted natural material resin on a dry basis (weight of pre-reacted natural material resin per weight of dry matter in the suspension) can be, e.g., from 0.1 wt. % or 0.2 wt. % or 0.3 wt. % or 0.5 wt. % to 0.7 wt. % or 1.0 wt. % or 1.8 wt. %.

In certain embodiments the epoxy is at least one member selected from the group consisting of epoxidized unsaturated oils such as epoxidized soybean oil, epoxidized vegetable oil, and the like; epoxidized alcohols such as isoborbide glycidyl ether, polyglycerol-3-glycidyl ether, castor oil glycidyl ether; epoxidized polysaccharides such as sorbitol polyglycidyl ether, EX-201: Resorcinol Diglycidyl Ether; EX-211: Neopentyl Glycol Diglycidyl Ether; EX-212: 1,6-Hexanediol Diglycidyl Ether; EX-252: Hydrogenated Bisphenol A Diglycidyl Ether; EX-313: Glycerol Polyglycidyl Ether; EX-314: Glycerol Polyglycidyl Ether; EX-321: Trimethylolpropane Polyglycidyl Ether; EX-411: Pentaerythritol Polyglycidyl Ether; EX-421: Diglycerol Polyglycidyl Ether; EX-512: Polyglycerol Polyglycidyl Ether; EX-612: Sorbitol Polyglycidyl Ether; EX-711: Diglycidyl Terephthalate; EX-721: Diglycidyl o-Phthalate; EX-731: N-Glycidyl Phthalimide; EX-810: Ethylene Glycol Diglycidyl Ether; EX-811: Ethylene Glycol Diglycidyl Ether; EX-850: Diethylene Glycol Diglycidyl Ether; EX-851: Diethylene Glycol Diglycidyl Ether; EX-821: Polyethylene Glycol Diglycidyl Ether; EX-920: Polypropylene Glycol Diglycidyl Ether; EM-160: Emulsion of Epoxy Cresol Novolac Resin; DENACOL FCA-640: Hexahydrophthalic acid diglycidyl ester; and the like, available from Nagase.

The epoxy is present in particles of the invention in an amount effective to react with the amine moiety, the isocyanate moiety, and/or the hydrolyzed organofunctional silane moieties. The amount of epoxy on a dry basis (weight of epoxy per weight of dry matter in the suspension) can be, e.g., from 0.1 wt. % or 0.7 wt. % or 1.0 wt. % or 1.5 wt. % to 2.0 wt. % or 2.5 wt. % or 3.6 wt. %.

In certain embodiments, the aldehyde comprises a member selected from the group consisting of aliphatic dialdehydes, aromatic dialdehydes, cyclic dialdehydes, and polyaldehydes. Nonlimiting examples of one or more aldehydes include, but are not limited to, valeraldehyde, capronaldehyde, capryladehyde, decanal, succinic dialdehyde, cyclohexanecarbaldehyde, cyclopentanecarbaldehyde, 2-methyl-1-propanal, 2-methylpropionaldehyde, acetaldehyde, acrolein, aldosterone, antimycin A, 8'-apo-µ-caroten-8'-al, benzaldehyde, butanal, chloral, citral, citronellal, crotonaldehyde, dimethylaminobenzaldehyde, folinic acid, fosmidomycin, furfural, glutaraldehyde, glutardialdehyde, glyceraldehyde, glycolaldehyde, glyoxal, glyoxylic acid, heptanal, 2-hydroxybenzaldehyde, 3-hydroxybutanal, hydroxymethylfurfural, 4-hydroxynonenal, isobutanal, isobutyraldehyde, methacrolein, 2-methylundecanal, mucochloric acid, N-methylformamide, 2-nitrobenzaldehyde, nonanal, octanal, oleocanthal, orlistat, pentanal, phenylethanal, phycocyanin, piperonal, propanal, propenal, protocatechualdehyde, retinal, salicylaldehyde, secologanin, streptomycin, strophanthidin, tylosin, vanillin, cinnamaldehyde glutaraldehyde, glyoxal, dialdehyde starch, polyethylene glycol dialdehyde, succinaldehyde, 1,3-propane dialdehyde, 1,4-butane dialdehyde, 1,5-pentane dialdehyde, dialdehyde starch, dialdehyde chitosan, reduced sugars containing aldehyde moieties, and the mixtures thereof.

The aldehyde is present in particles of the invention in an amount effective to react with the amine and/or hydrolyzed organofunctional silane moieties on the surface of the microcapsule and the amine or hydroxyl moiety on the natural material. The amount of aldehyde on a dry basis (weight of aldehyde per weight of dry matter in the suspension) can be, e.g., from 0.001 wt. % or 0.005 wt. % or 0.01 wt. % or 0.1 wt. % to 0.5 wt. % or 1.5 wt. % or 2.5 wt. %.

Cationic particles have a higher probability of adhering to anionic fabric in the laundering environment. Amine-functionality containing materials that can be incorporated into the spray-ready emulsion, which may have a favorable effect on adhesion of particles onto skin, hair, or fabric substrates comprise a polymer selected from the group consisting of polysaccharides, in one aspect, cationically modified starch and/or cationically modified guar; polysiloxanes; poly diallyl dimethyl ammonium halides; copolymers of poly diallyl dimethyl ammonium chloride and polyvinyl pyrrolidone; a composition comprising polyethylene glycol and polyvinyl pyrrolidone; acrylamides; imidazoles; imidazolinium halides; polyvinyl amine; copolymers of poly vinyl amine and N-vinyl formamide; polyvinylformamide, copolymers of polyvinylamine and polvyinylalcohol oligimers of amines, in one aspect a diethylenetriamine, ethylene diamine, bis(3-aminopropyl)piperazine, N,N-Bis-(3-aminopropyl) methylamine, tris(2-aminoethyl)amine and mixtures thereof; polyethyleneimime, a derivatized polyethyleneimine, in one aspect an ethoxylated polyethyleneimine; diester quaternary ammonium surfactants such as methyl bis-[ethyl(coconut)]-2-hydroxyethyl ammonium methyl sulfate, methyl bis-[ethyl(decyl)]-2-hydroxyethyl ammonium methyl sulfate, methyl bis-[ethyl(dodeceyl)]-2-hydroxyethyl ammonium methyl sulfate, methyl bis-[ethyl(lauryl)]-2-hydroxyethyl ammonium methyl sulfate, methyl bis-[ethyl(palmityl)]-2-hydroxyethyl ammonium methyl sulfate, methyl bis-[ethyl(soft-tallow)]-2-hydroxyethyl ammonium methyl sulfate, and the like; diester quat combined with laminate nanoclays such as laponite, bentonite, montmorillonite, and the like; chitosan with various degrees of deacetylation, carboxymethyl chitosans, glycol chitosans, whey protein, sodium caseinate, silk protein, 1H-Imidazolium, 1-ethenyl-3-methyl-, chloride, polymer with 1-ethenyl-2-pyrrolidinone, polyamines, polysaccharides with cationic modification, and mixtures thereof. Polysaccharides can be employed with cationic modification and alkoxy-cationic modifications, such as cationic hydroxyethyl, cationic hydroxy propyl. For example, cationic reagents of choice are 3-chloro-2-hydroxypropyl trimethylammonium chloride or its epoxy version. Furthermore, up to 5 different types of functional groups may be attached to the polysaccharides. Also, polymer graft chains may be differently modified than the backbone. The counterions can be any halide ion or organic counter ion. The preferred cationic starch has a molecular weight of from about 100,000 to about 500,000,000, preferably from about 200,000 to about 10,000,000 and most preferably from about 250,000 to about 5,000,000. The preferred cationic starch products are HI-CAT CWS42 and HI-CAT 02 and are commercially available from ROQUETTE AMERICA, Inc. The preferred cationic guar has a molecular weight of from about 50,000 to about 5,000,000. The preferred cationic guar products are Jaguar C-162 and Jaguar C-17 and are commercially available from Rhodia Inc.

The deposition aid is present in the controlled release particles in an amount on a dry basis (weight of deposition aid per weight of dry matter in the suspension) from 0.5 wt. % or 1 wt. % or 1.5 wt. % or 3.5 wt. % to 5 wt. % or 7 wt. % of the weight of the particle.

The controlled release particles are preferably spherical but non-spherical shapes are also within the scope of the invention. The particles preferably have a diameter from 0.05-250 microns, or from 0.1 microns to less than 100 microns.

Method of Making the Particles

The controlled release particles according to the present teaching are made in a multi-step process as described below. For convenience, the process is presented in the preferred mode which involves one aqueous phase composition and one hydrophobic oil phase composition. Nonetheless, those skilled in the art will readily appreciate that the aqueous phase composition may be prepared as a dual phase composition to which the hydrophobic oil phase composition is added or a three or more components composition where various ingredients are preferably isolated from one another until desired so as to avoid undue or undesired activation of the aqueous phase monomers or oligomers.

The hydrophobic oil phase composition is formed by combining the hydrophobic active core material with oil soluble monomers and oligomers. Most preferably this is conducted under moderate increased temperature so as to facilitate the solubilization or suspension of the monomers, oligomers, and other ingredients that may be present, including nucleating agents, in the core material. This is particularly useful if the core material is a solid or wax or a high viscosity material. Once again, if the temperature of the mixture had been elevated to aid in getting the hydrophobic oil phase monomer into solution/suspension, then the mixture should be cooled or allowed to cool to ambient temperature.

Materials that are not necessarily soluble or miscible in the oil phase can also be dispersed in the oil phase. The purpose is to maintain these materials at the oil-water interface to improve the properties of the membrane. In the present invention, polysaccharides, inorganic solid particles, basified biodegradable resins, pre-reacted natural material resin, and plasticizers are often materials that are not miscible in oil; however, they influence the barrier properties, flexibility, and biodegradability properties of the membrane.

The hydrophobic oil phase composition is added to an aqueous phase to form an emulsion. The mixture is agitated until the desired droplet size of oil phase composition is attained. In order to establish a wall at the oil-water interface, an amine is added to the aqueous phase followed by pH adjustment. Droplets are preferably from about 10 microns to about 75 microns, and more preferably from about 20 microns to about 50 microns in volume average diameter.

Not to be limited by theory, the amine added in the aqueous phase can react with several functional groups present in the hydrophobic oil phase, including isocyanate, epoxy, and organofunctional silane. The reactivity of amine is higher with isocyanate, and therefore provides a membrane via an interfacial polymerization reaction that limits the diffusion of the hydrophobic oil phase into the surrounding aqueous phase. Not to be limited by theory, the amine next reacts with epoxy functionality to form amino alcohols. The amino alcohols can in turn react with the isocyanates, such reaction will lead to the possible formation of polyurethanes and polyureas which will reduce the permeability of the membrane. Amines with multiple functional groups on the backbone are preferred since they offer the possibility to form a hydrophilic layer on the microcapsule surface, and provide the ability to link natural materials to the surface of the microcapsule. Such materials can be synthesized or can be realized via the byproducts of hydrolysis reactions. Preferred materials are selected from chemical structures represented by the following formulas:

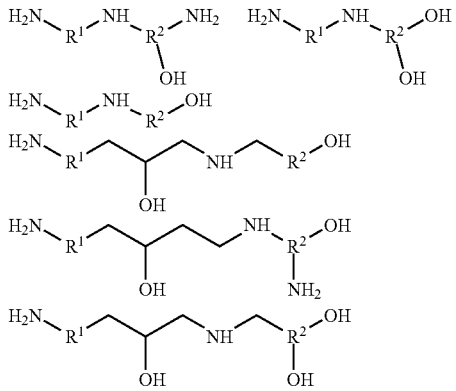

wherein $R^1$ is an alkyl chain of at least 3 carbon units or $C_6H_5$ or Silicon, and $R^2$ is an alkyl chain of 1 or 2 carbon units.

In other embodiments, the amine moiety containing material is preferably selected from chemical structures represented by the following formulas:

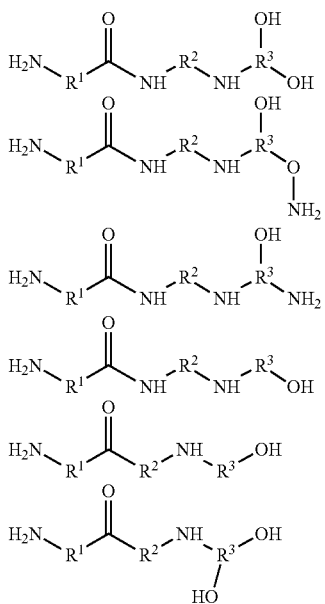

wherein $R^1$ is an alkyl chain of at least 3 carbon units or $C_6H_5$ or Silicon, $R^2$ is an alkyl chain of 1 or 2 carbon units, and $R^3$ is an alkyl chain of 1 or 2 carbon units.

In other embodiments, the amine moiety containing material is preferably selected from chemical structures represented by the following formulas:

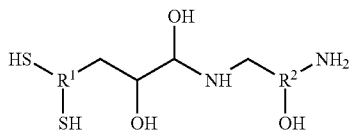

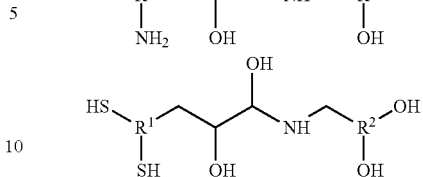

wherein $R^1$ is an alkyl chain of at least 3 carbon units or $C_6H_5$, and $R^2$ is an alkyl chain of 1 or 2 carbon units or Silicon.

The basified biodegradable resins already have amine functionalities; however, these amine functionalities may exist as carboxylate salts due to the zwitterionic effect. i.e. proteins have both amine functionality and acid functionality; hence the acids could be neutralized by the amines, or exist as a polyelectrolyte complex wherein the amine functionality is folded inward and unable to react with the isocyanate or epoxy functionalities. Basifying these materials reduces the zwitterionic effect, causes a desired unfolding of the protein material, and makes the amine more reactive. Not to be limited by theory, natural materials are generally inert and non-reactive. Pre-reacting such natural materials with epoxy, epoxide curing agent, or polyamide epicholorhydrin creates a covalent bond with specific functional groups of the natural material, and the pre-reacted polymer brings secondary amine functionalities. The secondary amines can further react with isocyanate and epoxy functionalities. Introduction of the hydrophobic oil phase into the aqueous phase can hydrolyze the organofunctional silanes. Such silanes self-condense in the presence of amine to form a cage structure comprising Si—O—Si bonds to reduce permeability of the membrane. In Type B particles, once the amine has reacted and is present on the surface of the particle, it can react with the copolymer of maleic anhydride to open up the anhydride ring to produce amide and carboxylate anion.

Inventors have discovered that pursuing a high degree of crosslinking in making polyurea, polyurethane, polyester, polyamide, poly(amine-alcohol), and the like, via chemical reaction processes that comprise interfacial polymerization, polycondensation reactions, addition reactions, free radial polymerization reactions, and the like, may provide a membrane with good barrier properties and mechanical properties; however, such membranes have poor environmental biodegradability. Not to be limited by theory, a high degree of crosslinking results in the absence of both functional groups and flexibility that hinders the ability of microbes to form a biofilm around the polymer membrane followed by digestion of membrane to improve biodegradability. Incorporation of biodegradable materials into the membrane via the use of basified biodegradable resins, sol-gel hydrogel forming materials, and pre-reacted natural material resin can improve barrier properties of the membrane (more tortuous path for the encapsulated material to diffuse, poor miscibility of the encapsulated active material in the polymer, biodegradable polymer segments swell with water reducing the diffusion of the encapsulated active), and improved environmental biodegradability of the membrane due to the presence of amino acids, glucose units, esters, amides, and other functional groups whose breakdown is enabled by enzymes that the microbes readily secrete.

Once this membrane is established, no further decrease in particle size of the oil droplets is observed. The reactor contents are agitated for 30 minutes to 5 hours, depending on the emulsifying properties of the hydrophobic oil phase. It is desired to maintain a temperature of the reactor below 40° C., in order to facilitate controlled membrane formation. It is desired to increase the temperature of the reactor contents to 60° C. for an additional 2 to 5 hours to complete the reaction.

In certain embodiments, the suspension of controlled release particles is dehydrated in order to expose the particles to a higher temperature to achieve a higher degree of crosslinking of the monomers.

In certain embodiments of providing a powder composition of the invention, or making the dehydrated forms of basified biodegradable resin, or making the pre-reacted natural material resin, spray drying is an economical process that can be used. Spray drying of the particle suspension is preferably conducted in a co-current spray dryer, at an inlet air temperature of 325 to 415° F. (163-213° C.), preferably from 355 to 385° F. (179-196° C.) and an outlet air temperature of 160 to 215° F. (71-101° C.), preferably from 175-195° F. (79-91° C.).

In certain powder composition embodiments, the silica flow aid is added to the dry powder to improve the flowability of the powder. Addition of the silica flow aid minimizes the agglomeration of particles during the heating, packing, and conveyance processes.

Advantages of at least some embodiments of the inventive method include at least one or at least two or at least three or at least four or at least five or at least six or all seven of the following:
a) Flexibility in active: membrane is developed at the oil-water interface via the use of interfacial polymerization;
b) Controlled permeability of the shell;
c) Controlled aggregation of the particles;
d) Functionalized surface to increase the adhesion or filtration efficiency of particles onto the substrate during a rinse-off process;
e) Favorable environmental biodegradability profile;
f) Can be used in a variety of applications, including but not limited to household care, personal care, beauty care, etc.; and/or
g) Preferably utilizes a commercially available, relatively inexpensive technique to further engineer the particle.

Compositions Containing the Particles

The invention further comprises compositions (e.g., products, articles of manufacture, etc.) comprising the controlled release particles. Such compositions include but are not limited baby care, beauty care, fabric & home care, family care, feminine care, health care, snack and/or beverage products or devices intended to be used or consumed in the form as sold, and not intended for subsequent commercial manufacture or modification. Such products include but are not limited to fine fragrances (e.g., perfumes, colognes eau de toilettes, after-shave lotions, pre-shave, face waters, tonics, and other fragrance-containing compositions for application directly to the skin), diapers, bibs, wipes; products for and/or methods relating to treating hair (human, dog, and/or cat), including, bleaching, coloring, dyeing, conditioning, shampooing, styling; deodorants and antiperspirants; personal cleansing; cosmetics; skin care including application of creams, lotions, and other topically applied products for consumer use; and shaving products, products for and/or methods relating to treating fabrics, hard surfaces and any other surfaces in the area of fabric and home care, including: air care, car care, dishwashing, fabric conditioning (including softening), laundry detergency, laundry and rinse additive and/or care, hard surface cleaning and/or treatment, and other cleaning for consumer or institutional use; products and/or methods relating to bath tissue, facial tissue, paper handkerchiefs, and/or paper towels; tampons, feminine napkins; products and/or methods relating to oral care including toothpastes, tooth gels, tooth rinses, denture adhesives, tooth whitening; over-the-counter health care including cough and cold remedies, pain relievers, RX pharmaceuticals, pet health and nutrition, and water purification; processed food products intended primarily for consumption between customary meals or as a meal accompaniment (non-limiting examples include potato chips, tortilla chips, popcorn, pretzels, corn chips, cereal bars, vegetable chips or crisps, snack mixes, party mixes, multigrain chips, snack crackers, cheese snacks, pork rinds, corn snacks, pellet snacks, extruded snacks and bagel chips); and coffee. Moreover, such products include, but are not limited to, a powdered food product, a fluid food product, a powdered nutritional supplement, a fluid nutritional supplement, a fluid fabric enhancer, a solid fabric enhancer, a fluid shampoo, a solid shampoo, hair conditioner, body wash, solid antiperspirant, fluid antiperspirant, solid deodorant, fluid deodorant, fluid detergent, solid detergent, fluid hard surface cleaner, solid hard surface cleaner, a fluid fabric refresher spray, a diaper, an air freshening product, a nutraceutical supplement, a controlled release fertilizer, a controlled release insecticide, a controlled release dye, and a unit dose detergent comprising a detergent and the controlled release particles in a water soluble film.

Fluid compositions of the invention preferably further comprise at least one suspension agent to suspend the controlled release particles, wherein the at least one suspension agent is at least one member selected from the group consisting of a rheology modifier, a structurant and a thickener. The at least one suspension agent preferably has a high shear viscosity at, 20 sec$^{-1}$ shear rate and at 21° C., of from 1 to 7000 cps and a low shear viscosity, at 0.5 sec$^{-1}$ shear rate and at 21° C., of greater than 1000 cps or 1000-200,000 cps. In certain embodiments, the composition has a high shear viscosity, at 20 sec$^{-1}$ and at 21° C., of from 50 to 3000 cps and a low shear viscosity, at 0.5 sec$^{-1}$ shear rate and at 21° C., of greater than 1000 cps or 1000-200,000 cps.

Preferably, the at least one suspension agent is selected from the group consisting of polyacrylates, polymethacrylates, polycarboxylates, pectin, alginate, gum arabic, carrageenan, gellan gum, xanthan gum, guar gum, gellan gum, hydroxyl-containing fatty acids, hydroxyl-containing fatty esters, hydroxyl-containing fatty waxes, castor oil, castor oil derivatives, hydrogenated castor oil derivatives, hydrogenated castor wax and mixtures thereof.

The invention further encompasses a slurry comprising particles of the invention. Said slurry may be combined with an adjunct ingredient to form a composition, for example, a consumer product. In certain embodiments, the slurry comprises at least one processing aid selected from the group consisting of water, aggregate inhibiting materials such as divalent salts, particle suspending polymers, and mixtures thereof. Examples of aggregate inhibiting materials include salts that can have a charge shielding effect around the particle, such as, e.g., magnesium chloride, calcium chloride, magnesium bromide, magnesium sulfate and mixtures thereof. Examples of particle suspending polymers include polymers such as xanthan gum, carrageenan gum, guar gum, shellac, alginates, chitosan; cellulosic materials such as carboxymethyl cellulose, hydroxypropyl methyl cellulose and cationically charged cellulosic materials; polyacrylic acid; polyvinyl alcohol; hydrogenated castor oil; ethylene glycol distearate; and mixtures thereof.

In certain embodiments, the slurry comprises at least one carrier selected from the group consisting of polar solvents, including but not limited to, water, ethylene glycol, propylene glycol, polyethylene glycol, glycerol, non-polar solvents including but not limited to mineral oil, perfume raw materials, silicone oils, hydrocarbon paraffin oils, and mixtures thereof.

In certain embodiments, a perfume oil is combined with the slurry comprising microcapsules to provide multiple benefits. The emulsified perfume oil will increase the viscosity of the slurry and prevent the phase separation of the microcapsule particles. The mixture provides a way to deliver non-encapsulated and encapsulated fragrance from the same slurry.

In certain embodiments, the composition has at least two controlled release technologies, which release different hydrophobic oil compositions and are selected from the group consisting of neat oils, friction-triggered release microcapsules and water-triggered release microcapsules.

The invention will be illustrated in more detail with reference to the following Examples, but it should be understood that the present invention is not deemed to be limited thereto.

EXAMPLES

Materials and Methods

The following is a representative perfume oil composition used for capsule making.

TABLE 1

| Perfume oil composition | | |
|---|---|---|
| Material | wt. % | Functionality |
| CITRONELLYL NITRILE | 1.00% | NITRILE |
| TRIPLAL | 0.25% | ALDEHYDE |
| FLORHYDRAL | 0.10% | ALDEHYDE |
| ALDEHYDE C-10 | 0.10% | ALDEHYDE |
| ALDEHYDE C-12 LAURIC | 0.20% | ALDEHYDE |
| ALLYL CYCLOHEXYL PROPIONATE | 1.00% | ESTER |
| CETALOX | 0.20% | FURAN |
| ANISIC ALDEHYDE | 0.10% | ALDEHYDE |
| CYCLACET | 10.00% | ESTER |
| CYCLAPROP | 5.00% | ESTER |
| DIHYDROMYRCENOL | 10.00% | ALCOHOL |
| DIPHENYL OXIDE | 1.00% | OXIDE |
| HABANOLIDE | 2.50% | KETONE |
| YARA YARA | 2.00% | ETHER |
| CIS-3-HEXENYL SALICYLATE | 2.00% | ESTER |
| VERDOX | 2.50% | ESTER |
| HEXYLCINNAMIC ALDEHYDE | 20.00% | ALDEHYDE |
| BHT | 0.50% | 0.0025 |
| ISO E SUPER | 2.50% | KETONE |
| KOAVONE | 2.50% | 0.0625 |
| EUCALYPTOL | 0.20% | ALCOHOL |
| MANZANATE, 10% IPM | 0.50% | ESTER |
| MUSCENONE, 10% IPM | 0.50% | KETONE |
| LAEVO CARVONE, 10% IPM | 0.50% | 0.0025 |
| METHYL ANTHRANILATE | 0.10% | ESTER |
| METHYL IONONE GAMMA | 1.25% | KETONE |
| LILIAL | 10.00% | ALDEHYDE |
| ALDEHYDE C-12 MNA, 10% DPG | 0.50% | ALDEHYDE |
| MYRAC ALDEHYDE | 0.50% | ALDEHYDE |
| D-LIMONENE | 5.00% | TERPENE |
| PEONILE | 2.50% | NITRILE |

TABLE 1-continued

| Perfume oil composition | | |
|---|---|---|
| Material | wt. % | Functionality |
| ETHYLENE BRASSYLATE | 12.50% | ESTER |
| PHENOXANOL | 2.50% | ALCOHOL |

Scanning Electron Microscopy

A Phenom Pure (Nanoscience Instruments Model PW-100-019) Scanning Electron Microscope is used to understand the particle morphology, and nature of particle deposits on fabrics. PELCO tabs carbon tape (12 mm OD, Ted Pella product number 16084-1) is applied to an aluminum specimen mount (Ted Pella Product No 16111). Next, the powder sample is placed onto the carbon tape using a transfer spatula. Excess powder is removed by blowing Dust-Off compressed gas onto the sample. The stub is then left in a desiccator under vacuum for 16 hours to flash off any volatiles. The sample is then placed into the Phenom Pure, and imaged to visualize particle morphology.

Detergent/Water Dissolution+Fabric Preparation

To 9.75 grams of a detergent solution (1 gram of liquid detergent added to 99 grams of water, then filtered through Whatman 597 filter catalog number 10311808) is added powder or slurry that achieves a concentration of approximately 1 wt. % perfume oil in the detergent solution. For water solubility, the powder is simply dosed into water rather than detergent solution. For the Detergent Dissolution Test, the sample is mixed at 200 RPM for 30 minutes at 33.3° C. A pre-weighed 3 inch diameter circle of black 100% cotton fabric is placed in a Buchner funnel attached to a vacuum line. 2 mL of the solution is then poured through the fabric, followed by a wash of 2 mL water. The fabric is allowed to air dry overnight.

Odor Evaluation

There are two techniques utilized to evaluate odor of fabrics:

1) The dried fabrics from the Detergent Dissolution Test+Fabric Preparation test are evaluated olfactively by a panel before and after rubbing. A subjective grading scale is used to grade fabrics before rubbing and after rubbing. In the case of before rubbing, the control that is used is a fabric treated with neat fragrance oil in the detergent solution. In the case of rubbed fabric, the control is the fabric before rubbing is performed.

TABLE 2

| Odor grading scale | |
|---|---|
| Odor Grade | Description |
| 0 | No Difference vs. Control |
| 1 | Slight Difference vs. Control |
| 2 | Noticeable Difference vs. Control (detectable difference) |
| 3 | Significant difference vs. control (high intensity vs. control) |
| 4 | Very High Intensity Bloom vs. control |
| 5 | Extremely High Intensity vs. Control |

The dried fabrics from the Detergent Dissolution Test+ Fabric Preparation test are evaluated by an Odor Meter (Shinyei Technology model OMX-SRM) before and after rubbing. This method reports the total concentration of volatiles in the headspace and is reported in milligrams per cubic meter as a function of time Leakage Stability A suspension of microcapsules is incorporated into Liquid Fabric Softener to deliver approximately 0.5 wt. % perfume usage level in the fabric softener. The mixture is aged 4 weeks at 40° C. in sealed glass jars. After aging, approximately 1.6 grams of the fabric softener mixture is diluted with 10 grams of water. 10 mL of isooctane is added to the vial, and the vial is inverted 10 times. 2-4 grams of sodium chloride is added to achieve a better separation. The sample is placed on a platform shaker for 10 minutes at 225-235 RPM agitation. After mixing, sample is centrifuged at 2800 RPM for 2 minutes. Approximately 5 mL of the isooctane layer is removed from the vial and filtered through a 0.45 micron syringe filter. 980 microliters of this filtrate is mixed with 20 microliters of internal standard in a 2 mL GC autosampler vial. The sample is analyzed by Gas Chromatography. GC conditions are shown in Table 3 below.

TABLE 3

GC CONDITIONS

| Gas Chromatography/Mass Spectrophotometer Conditions | |
|---|---|
| Capillary Column | DB-5MS, 30 meter, 0.25 μm film, ID = 0.25 mm |
| Carrier Gas | UHP Helium, 1.2 mL/min through the column |
| Injection Volume | 1.0 μL, Split, Split Ratio 8.0:1 |
| Injector Port Temperature | 250° C. |
| Oven Conditions | |
| Initial Temperature | 40° C. |
| Hold Time | 2 minutes |
| Ramp | 5° C./min |
| Final Temperature | 270° C. |
| Final Hold | 6 minutes |
| Total Run Time | 54.0 minutes |
| Mass Spectrophotometer Detector Conditions | |
| MS Source Temperature | 230° C. |
| MS Quad | 150° C. |
| Back Detector | 270° C. |
| Tune File | Atune.u |
| Scan Range | 40 to 600 amu |
| Solvent Delay | 4.5 minutes |

Calculate the average Response Factor of total area sum from standard calibration curve. See equation below:

$$RF = ((Ax)*(Cis)/((Ais)(Cx))$$

where:
AX=Area of the compound
CX=Standard Concentration (mg)
Ais=Area of the internal standard
Cis=Internal Standard Concentration (mg)
Calculate sample concentration (mg). See equation below:

$$CXs = (((Ax)*(Cis)/((Ais)(RFAVE)))*df$$

where:
AX=Area of the compound
CXs=Sample Concentration (mg)
Ais=Area of the internal standard
RFAVE=Average Response Factor
df=Sample Dilution By using the sample concentration (mg) of perfume oil found in the isooctane extract and dividing by the theoretical perfume dosed into the fabric softener, one can calculate the amount of perfume that has leaked out of the microcapsule during aging.

Biodegradability Test Method

Biodegradability testing is carried out according to protocol OECD 301D. The microcapsule membrane is isolated by going through the following steps: (1) Lyophilize the microcapusule slurry sample, (2) Methanol/toluene extraction of the lyophilized solids to assure less than 5% residual oil, (3) filtration of the solvent and extracted material, (4) vacuum drying at 60° C. and 0.3 torr for 24 hours, (5) water extraction of the vacuum dried powder to remove any water soluble components in the membrane, followed by filtration to recover the particles, (6) vacuum dry the powder to remove residual water at 0.3 torr for 1 day 60° C. The isolated polymer is then subjected to OECD 301D protocol, available at https://www.oecd.org/chemicalsafety/risk-assessment/1948209.pdf, with the following experimental conditions:
1) test substance concentration in the mineral medium is 5 mg/L
2) 300 mL Biological Oxygen Demand (BOD) bottles with glass stoppers are used
3) An incubator at 20° C. is used to age the samples in the dark
4) The mineral stock solutions as provided in the method are prepared
5) After letting the secondary effluent settle for at least 1 hour, a 10× (10 mL of secondary effluent is added to 90 mL of deionized water) secondary effluent is prepared with BOD water to make 100 mL total inoculum in a beaker. Then 0.5 mL of the 10× inoculum is added to each BOD bottle.
6) COD of the isolated polymer is measured using Hach kit The bottles are checked for dissolved oxygen at 0 days, 7, 14, 28, and 60 days. The percent degradation is analyzed via the calculations taught in the OECD 301D method.

Example 1. Polyacrylate and Polyurea Hybrid Capsule

The following capsules are prepared by free radical polymerization of acrylate monomers in situ with polyisocyanate-amine reaction to yield a hybrid organic wall. High temperature is required to make a membrane. The membrane does not have any additional coatings to provide enhanced barrier properties of the present invention.

Prepare Oil Phase: mix 60 g of Perfume oil, 1.18 g of urethane acrylate oligomer, 2.36 g of aromatic acid acrylate half ester,
516.3 g of polyisocyanate and 0.34 g of Vazo-68 respectively. Contents of the mixture are allowed to stir at room temperature using a magnetic stir bar at 100-150 rpm for 20 minutes.

Prepare Aqueous Phase: 210 grams of 5 wt. % aqueous solution of polyvinyl pyrrolidone is prepared Emulsion Formation: The prepared oil phase is added into the aqueous phase while agitating the aqueous phase using a Caframo BDC6015, 4-blade pitched agitator shaft 1" diameter, at 750 rpm for 25 minutes to form a premix emulsion. An aliquot is analyzed by optical microscopy to understand particle size of the emulsion. 2 grams of water borne silsesquioxane oligomer is added dropwise and the reaction mixture is allowed to stir for next 5 hr at room temperature. The reaction mixture is then heated to 85° C. for 4 hours, followed by overnight stirring while cooling the batch.

Example 2. Preparation of Pre-Reacted Natural Material Resin

P-CMS: 101.05 grams of carboymethyl starch (Patel Chem Industries) is dissolved in 1824 grams of distilled water at room temperature. The pH of the solution is adjusted to 8.0 using 10 wt. % hydrochloric acid. After 10 minutes of mixing, a homogeneous solution is obtained. Next, 160 grams of Polycup 9700 (Solenis) is added to the suspension. The homogeneous suspension is spray dried in a Bowen 3 ft diameter co-current spray drying tower using a 2-fluid nozzle at 70 psi air pressure, an inlet air temperature of 385° F. (196° C.) and an outlet temperature of 185° F. (85° C.). Dry powder with a median size of 19 microns is collected from the spray dryer. The powder is then heated at 110° C. for 30 minutes in an oven.

P-Casein: 150 grams of Casein (Naked Casein, amazon.com) is dissolved in 2850 grams of distilled water at room temperature. Approximately 22.5 grams of 10 wt. % sodium carbonate is added to achieve a pH of 8.0 Next, 128.2 grams of Polycup 9700 (Solenis) is added to the suspension. The homogeneous suspension is spray dried in a Bowen 3 ft diameter co-current spray drying tower using a 2-fluid nozzle at 70 psi air pressure, an inlet air temperature of 385° F. (196° C.) and an outlet temperature of 185° F. (85° C.). Dry powder with a median size of 19 microns is collected from the spray dryer. The powder is then heated at 110° C. for 30 minutes in an oven.

P-Chitosan Oligosaccharide: 100 grams of chitosan oligosaccharide (TCI Chemicals C2849) is dissolved in 900 grams of distilled water at room temperature. The pH of the solution is adjusted to 9 by adding approximately 300 grams of 10 wt. % sodium carbonate solution in water. Approximately 780 grams of this solution is preweighed into a beaker, and 400 grams of Polycup 9700 (Solenis) is added to yield a solution. The homogeneous suspension is spray dried in a Bowen 3 ft diameter co-current spray drying tower using a 2-fluid nozzle at 70 psi air pressure, an inlet air temperature of 385° F. (196° C.) and an outlet temperature of 185° F. (85° C.). Dry powder with a median size of 19 microns is collected from the spray dryer. The powder is then heated at 110° C. for 30 minutes in an oven.

P-Gelatin-Glycerin: 150 grams of Gelatin high bloom strength is dissolved in 1350 grams of water at 40° C. 31 grams of glycerin is added to the solution. Approximately 8.5 grams of a 20% solution [BY WEIGHT? BY VOLUME? OTHER?] of sodium carbonate is added to adjust the pH to 10.2. Approximately 81 grams of Polycup 9700 (Solenis) is added to yield a homogeneous solution. The homogeneous suspension is spray dried in a Bowen 3 ft diameter co-current spray drying tower using a 2-fluid nozzle at 70 psi air pressure, an inlet air temperature of 350° F. (177° C.) and an outlet temperature of 185° F. (85° C.). Dry powder with a median size of 19 microns is collected from the spray dryer. The powder is then heated at 110° C. for 60 minutes in an oven.

Example 3. Preparation of Biodegradable Microcapsules

Microcapsules according to the invention were prepared with two different natural materials. One with milk protein and another with a polysaccharide. Glutaraldehyde was used as the dialdehyde linking agent. A more detailed description of the capsule formulations is provided below:

TABLE 4

Microcapsule examples

| Example | Formulation Description |
|---|---|
| 3A | Hexamethylene diisocyanate, Polyisocyanate |
|   | Diepoxy of aliphatic dimer acid, |
|   | Sorbitol glycidyl ether |
|   | Tetraethyl orthosilicate |
|   | Xylene diamine, silicone amines |
|   | Ethylamine modified maltodextrin |
| 3B | Hexamethylene diisocyanate, Polyisocyanate |
|   | Diepoxy of aliphatic dimer acid, |
|   | Sorbitol glycidyl ether |
|   | Tetraethyl orthosilicate |
|   | Xylene diamine, silicone amines |
|   | Ethylamine modified maltodextrin |
|   | Milk protein |
|   | Glutaraldehyde |
| 3C | Hexamethylene diisocyanate, Polyisocyanate |
|   | Diepoxy of aliphatic dimer acid, |
|   | Sorbitol glycidyl ether |
|   | Tetraethyl orthosilicate |
|   | Xylene diamine, silicone amines |
|   | Ethylamine modified maltodextrin |
|   | Maltodextrin |
|   | Glutaraldehyde |
| 3D | Hexamethylene diisocyanate, Polyisocyanate |
|   | Diepoxy of aliphatic dimer acid, |
|   | Sorbitol glycidyl ether |
|   | Tetraethyl orthosilicate |
|   | Xylene diamine, silicone amines |
|   | Ethylamine modified maltodextrin |
|   | Corn protein |
|   | Glutaraldehyde |

Capsule making procedure generally comprises the following steps:

Prepare Oil Phase: Perfume oil, isocyanates, epoxies, and tetraethyl orthosilicate are mixed to yield a homogeneous solution.

Prepare Aqueous Phase: 125 g of 5 wt. % aqueous solution of polyvinyl pyrrolidone is prepared.

Emulsion Formation: The prepared oil phase and aqueous phase are mixed using a propeller mixer at 1100 rpm for 25 minutes to form a premix emulsion. An aliquot is analyzed by optical microscopy to understand particle size of the emulsion. An aqueous pre-mixture of amines is slowly added to the emulsion. The mixture is heated at 60° C. for 5 hours. Allow the contents to stir overnight. Adequate time (1 to 3 hours) is allowed to achieve equilibrium and adsorption of key materials to the oil/water interface so that further reaction of the membrane components can be performed. The microcapsule slurry has a median particle size of 30-45 microns, and a perfume concentration of 9%-12% in the aqueous suspension. Microcapsules in the aqueous slurry have 60%-85% core by weight.

Example 4. Leakage Stability and Performance Testing

Microcapsules slurries are formulated into liquid fabric softener (Downy Free & Clear), to deliver approximately 0.5 wt. % fragrance usage level in the liquid suspension, via the microcapsules or neat perfume oil. These samples are used for leakage stability testing and performance testing. The prepared mixtures are aged for 1 week at 40° C. After ageing, several tests are performed to evaluate the behavior of the capsules.

1) Optical microscopy to observe capsule deflation.
2) Approximately 5 grams of the aged mixture is diluted with 5 grams of water to yield a dilute detergent solution containing approximately 0.25 wt. % fragrance oil. This diluted suspension is mixed for 30 minutes at a temperature of 25° C. at 250 RPM using a magnetic stirrer. Next, approximately 2 mL of the mixed solution is filtered through a black fabric, and allowed to dry overnight. The fabric odor intensity before rubbing and after rubbing is noted.

TABLE 5

Fabric odor performance of microcapsule slurries aged in liquid fabric softener for 4 week at 40° C.

| ID | Description of Capsule | Odor Grading* Pre-Rub/Post-Rub | Leakage 4 wk/40° C. |
|---|---|---|---|
| Example 1 | Comparative Capsule | 0/3 | 51% |
| Example 4A | Example 3A Capsules | 0/2 | 14% |
| Example 4B | Example 3B Capsules | 0/4 | 12% |
| Example 4C | Example 3C Capsules | 0/2 | 22% |
| Example 4D | Example 3D Capsules | 0/4 | 10% |

| Pre-Rub or Post-Rub Odor Grade | Description |
|---|---|
| 0 | No odor |
| 1 | Slight odor |
| 2 | Noticeable odor |
| 3 | Highly Noticeable, obvious odor |
| 4 | Strong and highly impactful odor |

*Performance Grading Scale

Example 5. Environmental Biodegradability

Microcapsules of various examples above were evaluated for environmental biodegradability by adapting the OCDE/OECD 301D Closed Bottle Test method, as described in the Biodegradability test method description.

Microcapsule suspensions were lyophilized, then extracted with methanol/toluene to remove the encapsulated perfume oil (12:1 ratio), and filtered. After vacuum drying, the powder was extracted with water (15:1 ratio) and filtered. The powder was vacuum dried, ground into a fine powder using a mortar/pestle, and submitted for biodegradability testing.

TABLE 6.1

Mineral Oil Solutions

| Mineral Solution ID | Ingredient | Formula | Mass (g) |
|---|---|---|---|
| A | Potassium dihydrogen orthophosphate | $KH_2PO_4$ | 8.50 |
|   | Dipostassium hydrogen orthophosphate | $K_2HPO_4$ | 21.75 |
|   | Disodium hydrogen orthophosphate dehydrate | $Na_2HPO_4$—$2H_2O$ | 33.40 |
|   | Ammonium chloride Dissolve in water and bring to 1 L. pH to 7.4 | $NH_4Cl$ | 0.50 |
| B | Calcium Chloride anhydrous OR | $CaCl_2$ | 27.50 |
|   | Calcium Chloride dehydrate Dissolve in water and bring to 1 L. | $CaCl_2$—$2H_2O$ | 36.40 |
| C | Magnesium sulfate heptahydrate Dissolve in water and bring to 1 L. | $MgSO_4$—$7H_2O$ | 22.50 |
| D | Iron (III) chloride hexahydrate Dissolve in water and bring to 1 L. | $FeCl_3$—$6H_2O$ | 0.25 |

Prepare approximately 300 mL solutions containing the particles to be tested (approximately 1.5 milligrams of the isolated polymer is added to each BOD bottle). Fill BOD bottles (300 mL capacity) just past the neck of the bottle. Insert stopper. Store BOD bottles in the dark in an incubator maintained at 20° C. Use dissolved oxygen meter (YSI 5000), and YSI5905 Dissolved Oxygen meter probe to measure oxygen at specific time points.

The dissolved oxygen measured values as a function of time, and the calculation methods presented in OECD 301D method are utilized to calculate the % biodegradability. The Environmental Biodegradability index is calculated by multiplying the measured % biodegradability by 100. The results are listed in Table 6.2 below.

TABLE 6.2

Environmental Biodegradability Results

| Material/Attribute | OECD 301D % Biodegradability (28 day) | Biodegradability Index |
|---|---|---|
| Example 1 | 1% | 1 |
| Example 3A | 12% | 12 |
| Example 3B | 62% | 62 |
| Example 3C | 52% | 52 |
| Example 3D | 61% | 61 |

A biodegradability index greater than 60 meets current ECHA requirements for microplastics biodegradability (2019). We anticipate 3B, 3C, 3D, and 3E to continue to increase in biodegradability to 60% in 60 days.

Example 6—Hair Conditioner

Selected microcapsules from the above examples are formulated into a leave-on-conditioner formulation as follows: to 98.0 grams of leave-on-conditioner (with a typical formulation given below) is added an appropriate amount of microcapsule slurry of Example 3, to deliver an encapsulated oil usage level of 0.5 wt. %. The microcapsules are added on top of the conditioner formulation, then the contents are mixed at 1000 RPM for 1 minute.

A typical composition of a leave-on conditioner formulation is given in Table 6.3 below.

TABLE 6.3

Hair Condition Formulation

| Components | Ex. I (LOT) (%) |
|---|---|
| Premix | |
| Aminosilicone | — |
| PDMS | 1.0-1.5 |
| Gel matrix carrier | |
| Behenyl trimethyl ammonium chloride | — |
| Stearamidopropyldimethylamine (SAPDMA), C18 | 0.60-0.8 |
| DTDMAC, C18(Quaternium-18) | 0.45-0.6 |
| Citric Acid (anhydrous) | 0.10-0.25 |
| Cetyl alcohol | 0.80-1.0 |
| Stearyl alcohol | 0.54-1.0 |
| Deionized Water | Balance |
| Polymers | |
| Hydroxyethylcellulose (HEC) | 0.15-0.50 |
| PEG-2M (Polyox WAR N-10) | 0.30-0.60 |
| Others | |
| Preservatives | 0.40-0.60 |

Example 7—Shampoo

Selected microcapsules from the above examples are formulated into a rinse-off shampoo formulation as follows: to 90.0 grams of shampoo formulation is added an appropriate amount of microcapsule slurry of Examples 3, to deliver an encapsulated oil usage level of 0.5 wt. %. The microcapsules and water are added on top of the shampoo formulation, then the contents are mixed at 1850 RPM for 1 minute. Typical shampoo formulations are shown in Tables 7.1, 7.2 and 7.3 below.

TABLE 7.1

Shampoo Formulations of Examples 7A-7C.

| Ingredient | 7A | 7B | 7C |
|---|---|---|---|
| Water | q.s. | q.s. | q.s. |
| Polyquaternium 76 [1] | 2.50 | — | — |
| Guar, Hydroxylpropyl Trimonium Chloride [2] | — | 0.25 | — |
| Polyquaterium 6 [3] | — | — | 0.79 |
| Sodium Laureth Sulfate (SLE3S) [4] | 21.43 | 21.43 | 21.43 |
| Sodium Lauryl Sulfate (SLS) [5] | 20.69 | 20.69 | 20.69 |
| Silicone [6] | 0.75 | 1.00 | 0.5 |
| Cocoamidopropyl Betaine [7] | 3.33 | 3.33 | 3.33 |
| Cocoamide MEA [8] | 1.0 | 1.0 | 1.0 |
| Ethylene Glycol Distearate [9] | 1.50 | 1.50 | 1.50 |
| Sodium Chloride [10] | 0.25 | 0.25 | 0.25 |
| Fragrance | 0.70 | 0.70 | 0.70 |
| Fragrance Microcapsules | 1.2 | 1.2 | 1.2 |
| Preservatives, pH adjusters | Up to 1% | Up to 1% | Up to 1% |

[1] Mirapol AT-1, Copolymer of Acrylamide(AM) and TRIQUAT, MW = 1,000,000; CD = 1.6 meq./gram; 10% active ; Supplier Rhodia
[2] Jaguar C500, MW - 500,000, CD = 0.7, supplier Rhodia
[3] Mirapol 100S, 31.5% active, supplier Rhodia
[4] Sodium Laureth Sulfate, 28% active, supplier: P&G
[5] Sodium Lauryl Sulfate, 29% active supplier: P&G
[6] Glycidol Silicone VC2231-193C
[7] Tegobetaine F-B, 30% active supplier: Goldschmidt Chemicals
[8] Monamid CMA, 85% active, supplier Goldschmidt Chemical
[9] Ethylene Glycol Distearate, EGDS Pure, supplier Goldschmidt Chemical
[10] Sodium Chloride USP (food grade), supplier Morton; note that salt is an adjustable ingredient, higher or lower levels may be added to achieve target viscosity.

TABLE 7.2

Shampoo Formulations of Examples 7D-7F.

| Ingredient | 7D | 7E | 7F |
|---|---|---|---|
| Water | q.s. | q.s. | q.s. |
| Silicone A [1] | 1.0 | 0.5 | 0.5 |
| Cyclopentasiloxane [4] | — | 0.61 | 1.5 |
| Behenyl trimethyl ammonium chloride [5] | 2.25 | 2.25 | 2.25 |
| Isopropyl alcohol | 0.60 | 0.60 | 0.60 |
| Cetyl alcohol [6] | 1.86 | 1.86 | 1.86 |
| Stearyl alcohol [7] | 4.64 | 4.64 | 4.64 |
| Disodium EDTA | 0.13 | 0.13 | 0.13 |
| NaOH | 0.01 | 0.01 | 0.01 |
| Benzyl alcohol | 0.40 | 0.40 | 0.40 |
| Methylchloroisothiazolinone/ Methylisothiazolinone [8] | 0.0005 | 0.0005 | 0.0005 |
| Panthenol [9] | 0.10 | 0.10 | 0.10 |
| Panthenyl ethyl ether [10] | 0.05 | 0.05 | 0.05 |
| Fragrance | 0.35 | 0.35 | 0.35 |
| Fragrance Microcapsules | 1.2 | 1.2 | 1.2 |

[1] Glycidol Silicone
[4] Cyclopentasiloxane: SF1202 available from Momentive Performance Chemicals
[5] Behenyl trimethyl ammonium chloride/Isopropyl alcohol: Genamin ™ KMP available from Clariant
[6] Cetyl alcohol: Konol ™ series available from Shin Nihon Rika
[7] Stearyl alcohol: Konol ™ series available from Shin Nihon Rika
[8] Methylchloroisothiazolinone/Methylisothiazolinone: Kathon ™ CG available from Rohm & Haas
[9] Panthenol: Available from Roche
[10] Panthenyl ethyl ether: Available from Roche

TABLE 7.3

Shampoo Formulations of Examples 7G and 7H

| Ingredient | 7G | 7H |
|---|---|---|
| Sodium Laureth Sulfate | 10.00 | 10.00 |
| Sodium Lauryl Sulfate | 1.50 | 1.50 |
| Cocamidopropyl betaine | 2.00 | 2.00 |
| Guar Hydroxypropyl trimonium chloride [1] | 0.40 | |
| Guar Hydroxypropyl trimonium chloride [2] | | 0.40 |
| Dimethicone [3] | 2.00 | 2.00 |
| Gel Network [4] | | 27.27 |
| Ethylene Glycol Distearate | 1.50 | 1.50 |
| 5-Chloro-2-methyl-4-isothiazolin-3-one, Kathon CG | 0.0005 | 0.0005 |
| Sodium Benzoate | 0.25 | 0.25 |
| Disodium EDTA | 0.13 | 0.13 |
| Perfume | 0.40 | 0.40 |
| Fragrance Microcapsules | 0.30 | 0.30 |
| Citric Acid/Sodium Citrate Dihydrate | pH QS | pH QS |
| Sodium Chloride/Ammonium Xylene Sulfonate | Visc. QS | Visc. QS |
| Water | QS | QS |

[1] Jaguar C17 available from Rhodia
[2] N-Hance 3269 (with Mol. W. of ~500,000 and 0.8 meq/g) available from Aqulaon/Hercules
[3] Viscasil 330M available from General Electric Silicones
[4] Gel Networks; See composition in Table 7.4 below. The water is heated to about 74° C. and the Cetyl Alcohol, Stearyl Alcohol, and the SLES Surfactant are added to it. After incorporation, this mixture is passed through a heat exchanger where it is cooled to about 35° C. As a result of this cooling step, the Fatty Alcohols and surfactant crystallized to form a crystalline gel network.

TABLE 7.4

Gel Network Composition

| Ingredient | Wt. % |
|---|---|
| Water | 86.14% |
| Cetyl Alcohol | 3.46% |
| Stearyl Alcohol | 6.44% |
| Sodium laureth-3 sulfate | 3.93% |

TABLE 7.4-continued

Gel Network Composition

| Ingredient | Wt. % |
|---|---|
| (28% Active) 5-Chloro-2-methyl-4-isothiazolin-3-one, Kathon CG | 0.03% |

Example 8—Lotion

For the examples shown in Table 8 below, in a suitable container, combine the ingredients of Phase A. In a separate suitable container, combine the ingredients of Phase B. Heat each phase to 73° C.-78° C. while mixing each phase using a suitable mixer (e.g., Anchor blade, propeller blade, or IKA T25) until each reaches a substantially constant desired temperature and is homogenous. Slowly add Phase B to Phase A while continuing to mix Phase A. Continue mixing until batch is uniform. Pour product into suitable containers at 73-78° C. and store at room temperature. Alternatively, continuing to stir the mixture as temperature decreases results in lower observed hardness values at 21 and 33° C.

TABLE 8

Lotion Formulations (Examples 8A-8C).

| Ingredient/Property | Example 8A | Example 8B | Example 8C |
|---|---|---|---|
| PHASE A | | | |
| DC-9040 [1] | 8.60 | 3.00 | 5.00 |
| Dimethicone | 4.09 | 4.00 | 4.00 |
| Polymethylsilsesquioxane [2] | 4.09 | 4.00 | 4.00 |
| Cyclomethicone | 11.43 | 0.50 | 11.33 |
| KSG-210 [3] | 5.37 | 5.25 | 5.40 |
| Polyethylene wax [4] | 3.54 | | 2.05 |
| DC-2503 Cosmetic Wax [5] | 7.08 | 10.00 | 3.77 |
| Hydrophobic TiO$_2$ | | | 0.50 |
| Iron oxide coated Mica | | | 0.65 |
| TiO$_2$ Coated Mica | 1.00 | 1.00 | |
| Fragrance Microcapsules | 1.00 | 1.00 | 1.00 |
| PHASE B | | | |
| Glycerin | 10.00 | 10.00 | 10.00 |
| Dexpanthenol | 0.50 | 0.50 | 0.50 |
| Pentylene Glycol | 3.00 | 3.00 | 3.00 |
| Hexamidine Diisethionate [6] | 0.10 | 0.10 | 0.10 |
| Niacinamide [7] | 5.00 | 5.00 | 5.00 |
| Methylparaben | 0.20 | 0.20 | 0.20 |
| Ethylparaben | 0.05 | 0.05 | 0.05 |
| Sodium Citrate | 0.20 | 0.20 | 0.20 |
| Citric Acid | 0.03 | 0.03 | 0.03 |
| Sodium Benzoate | 0.05 | 0.05 | 0.05 |
| Sodium Chloride | 0.50 | 0.50 | 0.50 |
| FD&C Red #40 (1%) | 0.05 | 0.05 | 0.05 |
| Water | q.s to 100 | q.s to 100 | q.s to 100 |
| Hardness at 21° C. (g) | 33.3 | 15.4 | 14.2 |
| Hardness at 33° C. (g) | 6.4 | 0.7 | 4.0 |

[1] 12.5% Dimethicone Crosspolymer in Cyclopentasiloxane. Available from Dow Corning.
[2] E.g., TOSPEAR 145A or TOSPEARL 2000. Available from GE Toshiba Silicon.
[3] 25% Dimethicone PEG-10/15 Crosspolymer in Dimethicone. Available from Shin-Etsu.
[4] JEENATE 3H polyethylene wax from Jeen.
[5] Stearyl Dimethicone. Available from Dow Corning.
[6] Hexamidine diisethionate, available from Laboratoires Serobiologiques.
[7] Additionally or alternatively, the composition may comprise one or more other skin care actives, their salts and derivatives, as disclosed herein, in amounts also disclosed herein as would be deemed suitable by one of skill in the art.

Example 9—Antiperspirant/Deodorant

Example 9A of Table 9.1 below can be made via the following general process, which one skilled in the art will be able to alter to incorporate available equipment. The ingredients of Part I and Part II are mixed in separate suitable containers. Part II is then added slowly to Part I under agitation to assure the making of a water-in-silicone emulsion. The emulsion is then milled with a suitable mill, for example a Greeco 1L03 from Greeco Corp, to create a homogenous emulsion. Part III is mixed and heated to 88° C. until the all solids are completely melted. The emulsion is then also heated to 88° C. and then added to the Part 3 ingredients. The final mixture is then poured into an appropriate container, and allowed to solidify and cool to ambient temperature.

TABLE 9.1

Antiperspirant/Deodorant Formulation (Example 9A).

| Ingredient | Example 9A |
|---|---|
| Part I: Partial Continuous Phase | |
| Hexamethyldisiloxane[1] | QS |
| DC5200[2] | 1.20 |
| Fragrance | 0.35 |
| Fragrance Capsules | 1.00 |
| Part II: Disperse Phase | |
| Aluminum Chlorohydrate (40% solution) | 40.00 |
| propylene glycol | 5.00 |
| Water | 12.30 |
| Part III: Structurant Plus Remainder of Continuous Phase | |
| FINSOLVE TN | 6.50 |

QS—indicates that this material is used to bring the total to 100%.
[1] DC 246 fluid from Dow Corning
[2] from Dow Corning Examples 9B to 9E of Table 9.2 below can be made as follows: all ingredients except the fragrance, and fragrance capsules are combined in a suitable container and heated to about 85° C. to form a homogenous liquid. The solution is then cooled to about 62° C. and then the fragrance, and fragrance microcapsules are added. The mixture is then poured into an appropriate container and allowed to solidify up cooling to ambient temperature.

Example 9F of Table 9.2 can be made as follows: all the ingredients except the propellant are combined in an appropriate aerosol container. The container is then sealed with an appropriate aerosol delivery valve. Next air in the container is removed by applying a vacuum to the valve and then propellant is added to container through the valve. Finally an appropriate actuator is connected to the valve to allow dispensing of the product.

TABLE 9.2

Antiperspirant/Deodorant Formulations

| Ingredient | 9B | 9C | 9D | 9E | 9F |
|---|---|---|---|---|---|
| Product Form | Solid Deodorant | Solid Deodorant | Solid Deodorant | Solid Deodorant | Deodorant or Body Spray |
| dipropylene glycol | 45 | 22 | 20 | 30 | 20 |
| propylene glycol | 22 | 45 | 22 | | |
| tripopylene glycol | | | 25 | | |
| Glycerine | | | | 10 | |
| PEG-8 | | | | 20 | |
| ethanol | | | | | QS |
| Water | QS | QS | QS | QS | |
| sodium stearate | 5.5 | 5.5 | 5.5 | 5.5 | |
| tetra sodium EDTA | 0.05 | 0.05 | 0.05 | 0.05 | |
| sodium hydroxide | 0.04 | 0.04 | 0.04 | 0.04 | |
| triclosan | 0.3 | 0.3 | 0.3 | 0.3 | |
| Fragrance | 0.5 | 0.5 | 0.5 | 0.5 | 0.5 |
| Fragrance capsules | 1.0 | 1.0 | 1.0 | 1.0 | 0.5 |
| Propellant (1,1 difluoroethane) | | | | | 40 |

QS—indicates that this material is used to bring the total to 100%.

Example 10—Rinse-off Conditioner

The conditioning compositions of Examples 10A through 10F of Table 10 are prepared as follows: cationic surfactants, high melting point fatty compounds are added to water with agitation, and heated to about 80° C. The mixture is cooled down to about 50° C. to form a gel matrix carrier. Separately, slurries of perfume microcapsules and silicones are mixed with agitation at room temperature to form a premix. The premix is added to the gel matrix carrier with agitation. If included, other ingredients such as preservatives are added with agitation. Then the compositions are cooled down to room temperature.

The conditioning composition of Example 10B of Table 10 is prepared as follows: cationic surfactants, high melting point fatty compounds are added to water with agitation, and heated to about 80° C. The mixture is cooled down to about 50° C. to form a gel matrix carrier. Then, silicones are added with agitation. Separately, slurries of perfume microcapsules, and if included, other ingredients such as preservatives are added with agitation. Then the compositions are cooled down to room temperature.

TABLE 10

Rinse-Off Conditioner Formulations (Examples 10A-10F).

| Ingredient | 10A | 10B | 10C | 10D | 10E | 10F[3] |
|---|---|---|---|---|---|---|
| Premix | | | | | | |
| Aminosilicone-1[1] | 0.50 | 0.50 | | | | |
| Aminosilicone-2[2] | | | 0.50 | 0.50 | 0.50 | |
| PDMS | | | | | | 0.50 |
| Fragrance microcapsules | ... | 1.0 | 1.0 | 1.0 | 1.0 | 1.0 |
| Gel matrix carrier | | | | | | |
| Behenyl trimethyl ammonium chloride | 2.30 | 2.30 | 2.30 | 2.30 | 2.30 | 2.30 |
| Cetyl alcohol | 1.5 | 1.5 | 1.5 | 1.5 | 1.5 | 1.5 |
| Stearyl alcohol | 3.8 | 3.8 | 3.8 | 3.8 | 3.8 | 3.8 |
| Deionized Water | QS | QS | QS | QS | QS | QS |

TABLE 10-continued

Rinse-Off Conditioner Formulations (Examples 10A-10F).

| Ingredient | 10A | 10B | 10C | 10D | 10E | 10F[3] |
|---|---|---|---|---|---|---|
| Preservatives | 0.4 | 0.4 | 0.4 | 0.4 | 0.4 | 0.4 |
| Panthenol | — | — | 0.03 | — | — | — |
| Panthenyl ethyl ether | — | — | 0.03 | — | — | — |

[1] Aminosilicone-1 (AMD): having an amine content of 0.12-0.15 m mol/g and a viscosity of 3,000-8,000 mPa · s, which is water insoluble
[2] Aminosilicone-2 (TAS): having an amine content of 0.04-0.06 m mol/g and a viscosity of 10,000-16,000 mPa · s, which is water insoluble
[3] Comparative example with PDMS instead of amino silicone

Example 11—Body Cleansing Composition

The body cleaning compositions of Examples 11A-11C are prepared as follows.

The cleansing phase composition is prepared by adding surfactants, guars, and Stabylen 30 to water. Sodium chloride is then added to the mixture to thicken the cleansing phase composition. Preservatives and chelants are added to the formulation. Finally, perfume is added to the suspension.

The Benefit phase composition is prepared by mixing petrolatum and mineral oil to make a homogeneous mixture. Fragrance microcapsules are added to the suspension. Finally, the cleansing phase (e.g. surfactant phase) and benefit phase are mixed in different ratios to yield the body cleansing composition.

TABLE 11

Body Cleansing Composition Formulations (Examples 11A-11C).

| Ingredient | 11A | 11B | 11C |
|---|---|---|---|
| I: Cleansing Phase Composition | | | |
| Sodium Trideceth Sulfate (sulfated from Iconol TDA-3 (BASF Corp.) to >95% sulfate) | 5.9 | 5.9 | 5.9 |

TABLE 11-continued

Body Cleansing Composition Formulations (Examples 11A-11C).

| Ingredient | 11A | 11B | 11C |
|---|---|---|---|
| Sodium Lauryl Sulfate | 5.9 | 5.9 | 5.9 |
| Sodium Lauroamphoacetate (Cognis Chemical Corp.,) | 3.6 | 3.6 | 3.6 |
| Guar Hydroxypropyltrimonium Chloride (N-Hance 3196 from Aqualon) | — | 0.3 | 0.7 |
| Guar Hydroxypropyltrimonium Chloride (Jaguar C-17 from Rhodia) | 0.6 | — | — |
| Stabylen 30 (Acrylates/Vinyl Isodecanoate, 3V) | 0.33 | 0.33 | 0.33 |
| Sodium Chloride | 3.75 | 3.75 | 3.75 |
| Trideceth-3 (Iconal TDA-3 from BASF Corp.) | 1.75 | 1.75 | 1.75 |
| Methyl chloro isothiazolinone and methyl isothiazolinone (Kathon CG, Rohm & Haas) | 0.033 | 0.033 | 0.033 |
| EDTA (Dissolvine NA 2x) | 0.15 | 0.15 | 0.15 |
| Sodium Benzoate | 0.2 | 0.2 | 0.2 |
| Citric Acid, titrate | pH = 5.7 ± 0.2 | pH = 5.7 ± 0.2 | pH = 5.7 ± 0.2 |
| Perfume | 1.11% | 1.11% | 1.11% |
| Water and Minors (NaOH) | Q.S. | Q.S. | Q.S. |
| II: Benefit Phase Composition | | | |
| Petrolatum (G2218 from Sonnerbonn) | 60 | 60 | 60 |
| Mineral Oil (Hydrobrite 1000 from Sonnerbonn) | 20 | 20 | 20 |
| Fragrance Microcapsules | 10 | 10 | 10 |
| III: Surfactant Phase:Benefit Phase Blending Ratio | 50:50 | 90:10 | 90:10 |

Example 12—Fabric Softening Product

Non-limiting examples of product formulations containing purified perfume microcapsules of the aforementioned examples are summarized in the following table.

TABLE 12

Fabric Softening Product Formulations (Examples 12A-12J).

| Ingredient | 12A | 12B | 12C | 12D | 12E | 12F | 12G | 12H | 12I | 12J |
|---|---|---|---|---|---|---|---|---|---|---|
| FSA [a] | 14 | 16.47 | 14 | 12 | 12 | 16.47 | 3.00 | 6.5 | 5 | 5 |
| Ethanol | 2.18 | 2.57 | 2.18 | 1.95 | 1.95 | 2.57 | — | — | 0.81 | 0.81 |
| Isopropyl Alcohol | — | — | — | — | — | — | 0.33 | 1.22 | — | — |
| Microcapsule (% active)* | 0.6 | 0.75 | 0.6 | 0.75 | 0.37 | 0.60 | 0.37 | 0.6 | 0.37 | 0.37 |
| Phase Stabilizing Polymer [f] | 0.21 | 0.25 | 0.21 | 0.21 | 0.14 | — | — | 0.14 | — | — |
| Suds Suppressor [g] | — | — | — | — | — | — | — | 0.1 | — | — |
| Calcium Chloride | 0.15 | 0.176 | 0.15 | 0.15 | 0.30 | 0.176 | — | 0.1-0.15 | — | — |
| DTPA [h] | 0.017 | 0.017 | 0.017 | 0.017 | 0.007 | 0.007 | 0.20 | — | 0.002 | 0.002 |
| Preservative (ppm) [i,j] | 5 | 5 | 5 | 5 | 5 | 5 | — | 250 [j] | 5 | 5 |
| Antifoam [k] | 0.015 | 0.018 | 0.015 | 0.015 | 0.015 | 0.015 | — | — | 0.015 | 0.015 |
| Dye (ppm) | 40 | 40 | 40 | 40 | 40 | 40 | 11 | 30-300 | 30 | 30 |
| Ammonium Chloride | 0.100 | 0.118 | 0.100 | 0.100 | 0.115 | 0.115 | — | — | — | — |
| HCl | 0.012 | 0.014 | 0.012 | 0.012 | 0.028 | 0.028 | 0.016 | 0.025 | 0.011 | 0.011 |
| Structurant [l] | 0.01 | 0.01 | 0.01 | 0.01 | 0.01 | 10.01 | 0.01 | 0.01 | 0.01 | 0.01 |
| Neat Unencapsulated Perfume | 0.8 | 0.7 | 0.9 | 0.5 | 1.2 | 0.5 | 1.1 | 0.6 | 1.0 | 0.9 |
| Deionized Water | Balance | Balance | Balance | Balance | Balance | Balance | Balance | Balance | Balance | Balance |

[a] N,N-di(tallowoyloxyethyl)-N,N-dimethylammonium chloride.
[f] Copolymer of ethylene oxide and terephthalate having the formula described in U.S. Pat. No. 5,574,179 at col. 15, lines 1-5, wherein each X is methyl, each n is 40, u is 4, each R1 is essentially 1,4-phenylene moieties, each R2 is essentially ethylene, 1,2-propylene moieties, or mixtures thereof.
[g] SE39 from Wacker
[h] Diethylenetriaminepentaacetic acid.
[i] KATHON CG available from Rohm and Haas Co. "PPM" is "parts per million."
[j] Gluteraldehyde
[k] Silicone antifoam agent available from Dow Corning Corp. under the trade name DC2310.
[l] Hydrophobically-modified ethoxylated urethane available from Rohm and Haas under the tradename Aculyn ™ 44.
*Suitable microcapsules provided in Examples 3. (Percent active relates to the core content of the microcapsule)

Example 13—Dry Laundry Formulations

Non-limiting examples of product formulations containing purified perfume microcapsules of the aforementioned examples are summarized in the following table.

TABLE 13

Dry Laundry Formulations (Examples 13A-13G)

| Ingredient | 13A | 13B | 13C | 13D | 13E | 13F | 13G |
|---|---|---|---|---|---|---|---|
| Brightener | 0.1 | 0.1 | 0.1 | 0.2 | 0.1 | 0.2 | 0.1 |
| Soap | 0.6 | 0.6 | 0.6 | 0.6 | 0.6 | 0.6 | 0.6 |
| Ethylenediamine disuccinic acid | 0.1 | 0.1 | 0.1 | 0.1 | 0.1 | 0.1 | 0.1 |
| Acrylate/maleate copolymer | 1.5 | 1.5 | 1.5 | 1.5 | 1.5 | 1.5 | 1.5 |
| Hydroxyethane di(methylene phosphonic acid) | 0.4 | 0.4 | 0.4 | 0.4 | 0.4 | 0.4 | 0.4 |
| Mono-$C_{12-14}$ alkyl, di-methyl, mono-hydroyethyl quaternary ammonium chloride | 0.5 | 0.5 | 0.5 | 0.5 | 0.5 | 0.5 | 0.5 |
| Linear alkyl benzene | 0.1 | 0.1 | 0.2 | 0.1 | 0.1 | 0.2 | 0.1 |
| Linear alkyl benzene sulphonate | 10.3 | 10.1 | 19.9 | 14.7 | 10.3 | 17 | 10.5 |
| Magnesium sulphate | 0.4 | 0.4 | 0.4 | 0.4 | 0.4 | 0.4 | 0.4 |
| Sodium carbonate | 19.5 | 19.2 | 10.1 | 18.5 | 29.9 | 10.1 | 16.8 |
| Sodium sulphate | QS | QS | QS | QS | QS | QS | QS |
| Sodium Chloride | 0.1 | 0.1 | 0.1 | 0.1 | 0.1 | 0.1 | 0.1 |
| Zeolite | 9.6 | 9.4 | 8.1 | 18 | 10 | 13.2 | 17.3 |
| Photobleach particle | 0.1 | 0.1 | 0.2 | 0.1 | 0.2 | 0.1 | 0.2 |
| Blue and red carbonate speckles | 1.8 | 1.8 | 1.8 | 1.8 | 1.8 | 1.8 | 1.8 |
| Ethoxylated Alcohol AE7 | 1 | 1 | 1 | 1 | 1 | 1 | 1 |
| Tetraacetyl ethylene diamine agglomerate (92 wt. % active) | 0.9 | 0.9 | 0.9 | 0.9 | 0.9 | 0.9 | 0.9 |
| Citric acid | 1.4 | 1.4 | 1.4 | 1.4 | 1.4 | 1.4 | 1.4 |
| Polyethylene oxide | 0.2 | 0.2 | 0.2 | 0.2 | 0.2 | 0.2 | 0.2 |
| Enzymes e.g. Protease (84 mg/g active), Amylase (22 mg/g active) | 0.2 | 0.3 | 0.2 | 0.1 | 0.2 | 0.1 | 0.2 |
| Suds suppressor agglomerate (12.4 wt. % active) | 0.2 | 0.2 | 0.2 | 0.2 | 0.2 | 0.2 | 0.2 |
| Sodium percarbonate (having from 12% to 15% active AvOx) | 7.2 | 7.1 | 4.9 | 5.4 | 6.9 | 19.3 | 13.1 |
| Perfume oil | 0.5 | 0.5 | 0.5 | 0.5 | 0.5 | 0.5 | 0.5 |
| Solid perfume particles | 0.4 | 0 | 0.4 | 0.4 | 0.4 | 0.4 | 0.6 |
| Perfume microcapsules (Example 3) | 1.3 | 2.4 | 1 | 1.3 | 1.3 | 1.3 | 0.7 |
| Water | 1.4 | 1.4 | 1.4 | 1.4 | 1.4 | 1.4 | 1.4 |
| Misc | 0.1 | 0.1 | 0.1 | 0.1 | 0.1 | 0.1 | 0.1 |
| Total Parts | 100 | 100 | 100 | 100 | 100 | 100 | 100 |

QS—as used herein indicates that this material is used to bring the total to 100%.

Example 14—Liquid Laundry Formulations (HDLs)

Non-limiting examples of product formulations containing purified perfume microcapsules of the aforementioned examples are summarized in Tables 14.1, 14.2 and 14.3 below.

TABLE 14.1

Liquid Laundry Formulations (HDLs)

| Ingredient | 14A | 14B | 14C | 14D | 14E | 14F |
|---|---|---|---|---|---|---|
| Alkyl Ether Sulphate | 0.00 | 0.50 | 12.0 | 12.0 | 6.0 | 7.0 |
| Dodecyl Benzene Sulphonic Acid | 8.0 | 8.0 | 1.0 | 1.0 | 2.0 | 3.0 |
| Ethoxylated Alcohol | 8.0 | 6.0 | 5.0 | 7.0 | 5.0 | 3.0 |
| Citric Acid | 5.0 | 3.0 | 3.0 | 5.0 | 2.0 | 3.0 |
| Fatty Acid | 3.0 | 5.0 | 5.0 | 3.0 | 6.0 | 5.0 |

TABLE 14.1-continued

Liquid Laundry Formulations (HDLs)

| Ingredient | 14A | 14B | 14C | 14D | 14E | 14F |
|---|---|---|---|---|---|---|
| Ethoxysulfated hexamethylene diamine quaternized | 1.9 | 1.2 | 1.5 | 2.0 | 1.0 | 1.0 |
| Diethylene triamine penta methylene phosphonic acid | 0.3 | 0.2 | 0.2 | 0.3 | 0.1 | 0.2 |
| Enzymes | 1.20 | 0.80 | 0 | 1.2 | 0 | 0.8 |
| Brightener (disulphonated diamino stilbene based FWA) | 0.14 | 0.09 | 0 | 0.14 | 0.01 | 0.09 |
| Cationic hydroxyethyl cellulose | 0 | 0 | 0.10 | 0 | 0.200 | 0.30 |
| Poly(acrylamide-co-diallyldimethylammonium chloride) | 0 | 0 | 0 | 0.50 | 0.10 | 0 |
| Hydrogenated Castor Oil Structurant | 0.50 | 0.44 | 0.2 | 0.2 | 0.3 | 0.3 |
| Boric acid | 2.4 | 1.5 | 1.0 | 2.4 | 1.0 | 1.5 |
| Ethanol | 0.50 | 1.0 | 2.0 | 2.0 | 1.0 | 1.0 |
| 1,2 propanediol | 2.0 | 3.0 | 1.0 | 1.0 | 0.01 | 0.01 |
| Diethyleneglycol (DEG) | 1.6 | 0 | 0 | 0 | 0 | 0 |
| 2,3-Methyl-1,3-propanediol (M pdiol) | 1.0 | 1.0 | 0 | 0 | 0 | 0 |
| Mono Ethanol Amine | 1.0 | 0.5 | 0 | 0 | 0 | 0 |
| NaOH Sufficient To Provide Formulation pH of: | pH 8 | pH 8 | pH 8 | pH 8 | pH 8 | pH 8 |
| Sodium Cumene Sulphonate (NaCS) | 2.00 | 0 | 0 | 0 | 0 | 0 |
| Perfume | 0.7 | 0.5 | 0.8 | 0.8 | 0.6 | 0.6 |
| Polyethyleneimine | 0.01 | 0.10 | 0.00 | 0.10 | 0.20 | 0.05 |
| Perfume Microcapsules of Example 3 | 1.00 | 5.00 | 1.00 | 2.00 | 0.10 | 0.80 |
| Water | Balance to 100% | Balance to 100% | Balance to 100% | Balance to 100% | Balance to 100% | Balance to 100% |

TABLE 14.2

Liquid Laundry Detergent Formulations

| Ingredient | 14G | 14H | 14I | 14J |
|---|---|---|---|---|
| C14-C15 alkyl poly ethoxylate (8) | 6.25 | 4.00 | 6.25 | 6.25 |
| C12-C14 alkyl poly ethoxylate (7) | 0.40 | 0.30 | 0.40 | 0.40 |
| C12-C14 alkyl poly ethoxylate (3) sulfate Na salt | 10.60 | 6.78 | 10.60 | 10.60 |
| Linear Alkylbenzene sulfonate acid | 0.19 | 1.16 | 0.79 | 0.79 |
| Citric Acid | 3.75 | 2.40 | 3.75 | 3.75 |
| C12-C18 Fatty Acid | 4.00 | 2.56 | 7.02 | 7.02 |
| Enzymes | 0.60 | 0.4 | 0.60 | 0.60 |
| Boric Acid | 2.4 | 1.5 | 1.25 | 1.25 |
| Trans-sulphated ethoxylated hexamethylene diamine quat | 1.11 | 0.71 | 1.11 | 1.11 |
| Diethylene triamine penta methylene phosphonic acid | 0.17 | 0.11 | 0.17 | 0.17 |
| Fluorescent brightener | 0.09 | 0.06 | 0.14 | 0.14 |
| Hydrogenated Castor Oil | 0.05 | 0.300 | 0.20 | 0.20 |
| Ethanol | 2.50 | 1.00 | 2.50 | 2.50 |
| 1,2 propanediol | 1.14 | 0.7 | 1.14 | 1.14 |
| Sodium hydroxide | 3.8 | 2.6 | 4.60 | 4.60 |
| Mono Ethanol Amine | 0.8 | 0.5 | | |
| Na Cumene Sulphonate | | | 1.0 | |
| Dye | 0.002 | 0.002 | 0.002 | 0.002 |
| Opacifier (Styrene Acrylate based) | 0.1 | | | |
| Bentonite Softening Clay | | 1.0 | | |
| Polyquaternium 10 - Cationic hydroxyl ethyl cellulose | 1.0 | | 1.0 | 1.0 |
| PP-5495 (silicone ex Dow Corning Corporation, Midland, MI) | | 1.0 | | |
| DC 1664 (silicone ex Dow Corning Corporation, Midland, MI) | | | 1.0 | |
| Perfume micro capsules (expressed as perfume oil) of Example 3 | 0.8 | 0.5 | 1.0 | 0.7 |
| Perfume | 0.7 | 0.55 | 1.00 | 1.00 |
| Poly Ethylene Imine MW 25000 | 0.1 | | | |
| Water | Up to 100 | Up to 100 | Up to 100 | Up to 100 |

TABLE 14.3

Liquid Laundry Detergent Formulations.

| Ingredient | 14K | 14L | 14M |
|---|---|---|---|
| C14-C15 alkyl poly ethoxylate (8) | 3.7 | | 20.7 |
| C12-C14 alkyl poly ethoxylate (7) | | 16.7 | |
| C12-C14 alkyl poly ethoxylate (3) sulfate Na salt | 17.8 | | 5.5 |
| Linear Alkylbenzene sulfonate acid | 12.5 | 22.9 | 13.5 |
| Citric Acid | 3.9 | | 1.7 |
| C12-C18 Fatty Acid | 11.1 | 18 | 5.1 |
| Enzymes | 3 | 1.2 | 3 |
| Boric Acid | 0.5 | | 0.5 |
| Trans-sulphated ethoxylated hexamethylene diamine quat | 3.25 | | 1.2 |
| PEI 600 EO20 | 1.25 | | 1.2 |
| Diethylene triamine penta methylene phosphonic acid or HEDP | 1.6 | | 0.85 |
| Fluorescent brightener | 0.2 | 0.3 | 0.14 |
| Hydrogenated Castor Oil | | 0.2 | |
| 1,2 propanediol | 4.3 | 20.3 | 11.7 |
| Sodium hydroxide | | 1.0 | 3.9 |
| Mono Ethanol Amine | 9.8 | 6.8 | 3.1 |
| Dye | Present | Present | Present |
| PDMS | | 2.15 | |
| Potassium sulphite | | 0.2 | |
| Perfume micro capsules (expressed as perfume oil) of Examples 3 | 1.6 | 1.5 | 1.4 |
| Perfume | 1.2 | 1.6 | 1.0 |
| Form. Phenyl Boronic Acid | | | Present |
| Water** | Up to 100 | Up to 100 | Up to 100 |

**Low water liquid detergent in Polyvinylalcohol unidose/sachet

Example 15—Liquid and Gel Detergents

Non-limiting examples of product formulations containing purified perfume microcapsules of the aforementioned examples are summarized in Table 15 below.

TABLE 15

Liquid and Gel Detergent Formulations (% by Weight)

| Ingredient | 15A | 15B | 15C |
|---|---|---|---|
| Alkylbenzenesulfonic acid | 17.2 | 12.2 | 23 |
| C12-14 alcohol 7-ethoxylate | 8.6 | 0.4 | 19.5 |
| C14-15 alcohol 8-ethoxylate | — | 9.6 | — |
| C12-14 alcohol 3-ethoxylate sulphate, Na salt | 8.6 | — | — |
| C8-10 Alkylamidopropyldimethyl amine | — | — | 0.9 |
| Citric acid | 2.9 | 4.0 | — |
| C12-18 fatty acid | 12.7 | 4.0 | 17.3 |
| Enzymes | 3.5 | 1.1 | 1.4 |
| Ethoxylated polyimine | 1.4 | — | 1.6 |
| Ethoxylated polyimine polymer, quaternized and sulphated | 3.7 | 1.8 | 1.6 |
| Hydroxyethane diphosphonic acids (HEDP) | 1.4 | — | — |
| Pentamethylene triamine pentaphosphonic acid | — | 0.3 | — |
| Catechol 2,5 disulfonate, Na salt | 0.9 | — | — |
| Fluorescent whitening agent | 0.3 | 0.15 | 0.3 |
| 1,2 propandiol | 3.5 | 3.3 | 22 |
| Ethanol | — | 1.4 | — |
| Diethylene glycol | — | 1.6 | — |
| 1-ethoxypentanol | 0.9 | — | — |
| Sodium cumene sulfonate | — | 0.5 | — |
| Monoethanolamine (MEA) | 10.2 | 0.8 | 8.0 |
| MEA borate | 0.5 | 2.4 | — |
| Sodium hydroxide | — | 4.6 | — |
| Perfume | 1.6 | 0.7 | 1.5 |
| Perfume microcapsules as Example 3 | 1.1 | 1.2 | 0.9 |
| Water | 22.1 | 50.8 | 2.9 |
| Perfume, dyes, miscellaneous minors | Balance | Balance | Balance |
| Undiluted viscosity $(V_n)$ at 20 $s^{-1}$, cps | 2700 | 400 | 300 |

Example 16—Liquid Unit Dose

The following are examples of unit dosage forms wherein the liquid composition is enclosed within a PVA film. The preferred film used in the present examples is Monosol M8630 76 μm thickness.

TABLE 16

Unit Dose Laundry Cleaner

| | 16A 3 compartments | | | 16B 2 compartments | | 16C 3 compartments | | |
|---|---|---|---|---|---|---|---|---|
| Compartment # | 42 | 43 | 44 | 45 | 46 | 47 | 48 | 49 |
| Dosage (g) | 34.0 | 3.5 | 3.5 | 30.0 | 5.0 | 25.0 | 1.5 | 4.0 |
| Ingredients | Weight % | | | | | | | |
| Alkylbenzene sulfonic acid | 20.0 | 20.0 | 20.0 | 10.0 | 20.0 | 20.0 | 25 | 30 |
| Alkyl sulfate | | | | 2.0 | | | | |
| $C_{12-14}$ alkyl 7-ethoxylate | 17.0 | 17.0 | 17.0 | | 17.0 | 17.0 | 15 | 10 |
| $C_{12-14}$ alkyl ethoxy 3 sulfate | 7.5 | 7.5 | 7.5 | | | 7.5 | 7.5 | |
| Citric acid | 0.5 | | 2.0 | 1.0 | | | | 2.0 |
| Zeolite A | | | | 10.0 | | | | |
| $C_{12-18}$ Fatty acid | 13.0 | 13.0 | 13.0 | | 18.0 | 18.0 | 10 | 15 |
| Sodium citrate | | | | 4.0 | 2.5 | | | |
| Enzymes | 0-3 | 0-3 | 0-3 | 0-3 | | 0-3 | 0-3 | 0-3 |
| Sodium Percarbonate | | | | 11.0 | | | | |
| TAED | | | | 4.0 | | | | |

TABLE 16-continued

Unit Dose Laundry Cleaner

| | Example | | | | | | | |
|---|---|---|---|---|---|---|---|---|
| | 16A<br>3 compartments | | | 16B<br>2 compartments | | 16C<br>3 compartments | | |
| | Compartment # | | | | | | | |
| | 42 | 43 | 44 | 45 | 46 | 47 | 48 | 49 |
| | Dosage (g) | | | | | | | |
| | 34.0 | 3.5 | 3.5 | 30.0 | 5.0 | 25.0 | 1.5 | 4.0 |
| Ingredients | Weight % | | | | | | | |
| Polycarboxylate | | | | 1.0 | | | | |
| Ethoxylated Polyethylenimine[1] | 2.2 | 2.2 | 2.2 | | | | | |
| Hydroxyethane diphosphonic acid | 0.6 | 0.6 | 0.6 | 0.5 | | | 2.2 | |
| Ethylene diamine tetra(methylene phosphonic) acid | | | | | | 0.4 | | |
| Brightener | 0.2 | 0.2 | 0.2 | 0.3 | | 0.3 | | |
| Microcapsules Example 3 | 0.4 | 1.2 | 1.5 | 1.3 | 1.3 | 0.4 | 0.12 | 0.2 |
| Water | 9 | 8.5 | 10 | 5 | 11 | 10 | 10 | 9 |
| CaCl2 | | | | | | | 0.01 | |
| Perfume | 1.7 | 1.7 | | 0.6 | | 1.5 | 0.5 | |
| Minors (antioxidant, sulfite, aesthetics, . . . ) | 2.0 | 2.0 | 2.0 | 4.0 | 1.5 | 2.2 | 2.2 | 2.0 |
| Buffers (sodium carbonate, monoethanolamine) [2] | To pH 8.0 for liquids<br>To RA >5.0 for powders | | | | | | | |
| Solvents (1,2 propanediol, ethanol), sodium sulfate | To 100p | | | | | | | |

[1]Polyethylenimine (MW = 600) with 20 ethoxylate groups per —NH.
[2]RA = Reserve Alkalinity (g NaOH/dose)

While the invention has been described in detail and with reference to specific examples thereof, it will be apparent to one skilled in the art that various changes and modifications can be made therein without departing from the spirit and scope thereof.

What is claimed is:

1. A method for preparing a composition comprising controlled release particles, said method comprising the sequential steps of:
   (a) preparing an oil phase, wherein the oil phase comprises:
      (i) at least one hydrophobic active ingredient, at least one isocyanate, at least one epoxy, at least one organofunctional silane, and optionally a plasticizer; or
      (ii) at least one hydrophobic active ingredient, at least one isocyanate, at least one epoxy, at least one organofunctional silane, at least one pre-reacted natural material resin, and optionally a plasticizer;
   (b) preparing an aqueous phase comprising an emulsifier;
   (c) combining the oil phase and the aqueous phase to emulsify the at least one hydrophobic active ingredient and to provide an aqueous suspension of the at least one hydrophobic active ingredient;
   (d) adding to the aqueous suspension at least one amine moiety containing material to react with the at least one isocyanate, the at least one epoxy, or the at least one organofunctional silane to provide a barrier;
   (e) heating the aqueous suspension;
   (f) adding a natural material to the aqueous suspension to provide a microcapsule having hydroxyl moieties or amine moieties on a surface thereof;
   (g) adding an aldehyde to the aqueous suspension to react with the hydroxyl moieties or amine moieties on the surface of the microcapsule; and
   (h) adding structuring agents to the aqueous suspension to provide the controlled release particles homogeneously suspended in an aqueous dispersion.

2. The method of claim 1, wherein the emulsifier is a member selected from the group consisting of polyalkylene glycol ether; polyvinyl acetate; copolymers of polyvinyl acetate; polyacrylamide; poly(N-isopropylacrylamide); poly(2-hydroxypropyl methacrylate); poly(2-ethyl-2-oxazoline); poly(2-isopropenyl-2-oxazoline-co-methyl methacrylate); poly(methyl vinyl ether); polyvinyl pyrrolidone; copolymers of polyvinyl pyrrolidone; 1H-Imidazolium, 1-ethenyl-3-methyl-, chloride; polymer with 1-ethenyl-2-pyrrolidinone; vinyl acetate; colloidal silica; palmitamidopropyltrimonium chloride; distearyl dimonium chloride; cetyltrimethy lammonium chloride; quaternary ammonium compounds; aliphatic ammonium halides; alkyldimethyl benzylammonium halides; alkyldimethylethylammonium halides; poly(2-dimethylamino)ethyl methacrylate)methy 1 chloride quaternary salt; poly(l-vinylpyrrolidone-co-2-dimethylaminoethyl methacrylate); poly(acrylamide-co-diallyldimethylammonium chloride); and polybis(2-chloroethyl)ether-alt-1,3-bis (3-(dimethylamino)propylurea quaternized.

3. The method of claim 1, wherein step (d) is conducted for 0.5 to 2 hours at room temperature, step (e) comprises increasing a temperature of the aqueous suspension to 35° C., reacting for 1 to 3 hours, then increasing the temperature to 60° C. and reacting for 3 to 6 hours.

4. The method of claim 1, wherein the at least one amine moiety containing material is at least one member selected from the group consisting of linear aliphatic amines, aromatic amines, silicone amines, branched amines, polypeptides, polyamines, polyetheramines, and amino acids.

5. The method of claim 1, wherein the at least one isocyanate is at least one member selected from the group consisting of aliphatic isocyanates, aromatic isocyanates, polymeric isocyanates, cyclic isocyanates, hydrophilic isocyanates, hydrophobic isocyanates, isocyanurates, waterborne isocyanates and urethane acrylates containing isocyanate functionalities.

6. The method of claim 1, wherein the at least one organofunctional silane is at least one member selected from the group consisting of alkoxylated silane, trialkoxy silanes, functionalized trialkoxysilanes, tetraalkoxylated silanes and 1,2-bis(triethyxysilyl)ethane.

7. The method of claim 1, wherein the at least one epoxy is at least one member selected from the group consisting of epoxidized unsaturated oils, epoxidized alcohols and epoxidized polysaccharides.

8. The method of claim 1, wherein the natural material comprises a member selected from the group consisting of polypeptide, protein, polysaccharide, oligosaccharide, cellulose, polyphenol and lipid.

9. The method of claim 1, wherein the aldehyde comprises a member selected from the group consisting of aliphatic dialdehydes, aromatic dialdehydes, cyclic dialdehydes, and polyaldehydes.

10. The method of claim 1, wherein the at least one pre-reacted natural material resin is included in the oil phase and is a spray dried composite of a polyamide epichlorohydrin and an additional natural material, said spray dried composite formed by curing a spray dried particle at elevated temperature to crosslink the polyamide epichlorohydrin material with amine, hydroxyl, carboxyl, and/or thiol functionalities of at least one member selected from the group consisting of monosaccharides, oligosaccharides, polysaccharides, amino acids, proteins, celluloses, carboxy modified saccharides and mixtures thereof.

11. The method of claim 10, wherein the at least one pre-reacted natural material resin comprises a polymer having a weight ratio of the polyamide epichlorohydrin to the additional natural material of 1:99.

12. The method of claim 1, wherein the plasticizer is included in the oil phase and is at least one member selected from the group consisting of methyl esters of rosin, polyazelate esters, di-fatty acid esters, citrate esters, polyadipate esters and polyester resins consisting of inner and intra-esters of polyhydroxy carboxylic acids.

13. The method of claim 1, wherein the controlled release particles have a diameter from 0.1 microns to less than 200 microns.

14. The method of claim 1, wherein the composition is a powdered food product, a fluid food product, a powdered nutritional supplement, a fluid nutritional supplement, a fluid fabric enhancer, a solid fabric enhancer, a fluid shampoo, a solid shampoo, a hair conditioner, a body wash, a solid antiperspirant, a fluid antiperspirant, a solid deodorant, a fluid deodorant, a fluid detergent, a solid detergent, a fluid hard surface cleaner, a solid hard surface cleaner, a fluid fabric refresher spray, a diaper, an air freshening product, a nutraceutical supplement, a controlled release fertilizer, a controlled release insecticide, a controlled release dye or a unit dose detergent comprising a detergent and the controlled release particles in a water soluble film.

15. The method of claim 14, wherein at least one suspension agent is included in the composition to suspend the controlled release particles, wherein the at least one suspension agent is at least one member selected from the group consisting of a rheology modifier, a structurant and a thickener.

16. The method of claim 15, wherein the at least one suspension agent has a high shear viscosity, at 20 sec$^{-1}$ shear rate and at 21° C., of from 1 to 7000 cps and a low shear viscosity, at 0.5 sec$^{-1}$ shear rate and at 21° C., of greater than 1000 cps.

17. The method of claim 15, wherein the at least one suspension agent is a fluid having a high shear viscosity, at 20 sec$^{-1}$ shear rate and at 21° C., of from 50 to 3000 cps and a low shear viscosity, at 0.5 sec$^{-1}$ shear rate and at 21° C., of greater than 1000 cps.

18. The method of claim 16, wherein the at least one suspension agent is a member selected from the group consisting of polyacrylates, polymethacrylates, polycarboxylates, pectin, alginate, gum arabic, carrageenan, gellan gum, xanthan gum, guar gum, gellan gum, hydroxyl-containing fatty acids, hydroxyl-containing fatty esters, hydroxyl-containing fatty waxes, castor oil, castor oil derivatives, hydrogenated castor oil derivatives, hydrogenated castor wax, perfume oil, and mixtures thereof.

19. The method of claim 1, wherein the composition comprises two different controlled release particles which are friction-triggered release microcapsules which release the at least one hydrophobic active ingredient at different rates due to a difference in shell material friability or core material viscosity.

20. The method of claim 1, wherein the at least one hydrophobic active ingredient comprises a mixture of a hydrophobic active and a material selected from the group consisting of brominated oils, epoxidized oils, highly nonpolar oils, hydrophobically modified inorganic particles, nonionic emulsifiers and oil thickening agents.

21. The method of claim 1, wherein the composition has an Environmental Biodegradability greater than 50%.

22. The method of claim 1, wherein the at least one pre-reacted natural material resin is included in the oil phase and is a bulk reaction product of an epoxy or epoxide curing agent and an additional natural material, said composite formed by reacting the epoxy or epoxide curing agent with the additional natural material in a reactor at elevated temperature to crosslink the epoxy or epoxide curing agent with an amine functionality or an acid functionality of the additional natural material, which comprises at least one member selected from the group consisting of amino acids, proteins, carboxy modified saccharides, and mixtures thereof.

23. The method of claim 22, wherein the at least one pre-reacted natural material resin comprises a polymer having a weight ratio of the epoxy or epoxide curing agent to the additional natural material of 1:99.

* * * * *